(12) United States Patent
Murken

(10) Patent No.: US 6,607,546 B1
(45) Date of Patent: Aug. 19, 2003

(54) NASAL CATHETER

(76) Inventor: Roger E. Murken, 1330 San Bernardino Rd., Upland, CA (US) 91786

( * ) Notice: Subject to any disclaimer, the term of this patent is extended or adjusted under 35 U.S.C. 154(b) by 510 days.

(21) Appl. No.: 09/653,933

(22) Filed: Sep. 1, 2000

(51) Int. Cl.$^7$ .............................................. A61M 29/00
(52) U.S. Cl. ...................... 606/196; 606/199; 606/198
(58) Field of Search ................................. 606/199, 196, 606/198; 128/207.18, DIG. 26; 604/94.01, 174

(56) References Cited

U.S. PATENT DOCUMENTS

| | | | | |
|---|---|---|---|---|
| 4,102,342 | A | * 7/1978 | Akiyama et al. | 606/192 |
| 4,338,941 | A | * 7/1982 | Payton | 606/196 |
| 4,820,266 | A | * 4/1989 | Berry | 604/11 |
| 5,139,510 | A | * 8/1992 | Goldsmith et al. | 606/196 |
| 5,269,296 | A | * 12/1993 | Landis | 128/207.18 |
| 5,546,964 | A | * 8/1996 | Stangerup | 128/898 |
| 5,584,822 | A | * 12/1996 | Lively et al. | 604/286 |
| 5,599,304 | A | * 2/1997 | Shaari | 604/94.01 |
| 5,899,918 | A | * 5/1999 | Knott et al. | 606/204 |
| 6,027,478 | A | * 2/2000 | Katz | 604/102.01 |
| 6,093,169 | A | * 7/2000 | Cardoso | 604/94.01 |

OTHER PUBLICATIONS

Brochure for Xomed Rhinology Products Featuring Merocel Sponge Author–Xomed Rhinology Products; Revised Feb. 1997.

* cited by examiner

*Primary Examiner*—Danny Worrell
*Assistant Examiner*—Robert H. Muromoto, Jr.
(74) *Attorney, Agent, or Firm*—John K. Park; Park & Sutton LLP

(57) ABSTRACT

The nasal catheter system will provide an improvement over existing devices that do not fill the recesses of the nose, do cause significant pain and still do not stop nosebleeds very effectively. The objectives are achieved through the design of a version of the device that has two inflatable bags, which in the preferred embodiment are not elastic balloons. The anterior bag is much larger in volume than the anterior nasal cavity. The design of the bag is generally cylindrical but has deep ridges projecting outward producing a "pleated" design with ribs running along and parallel to the axis of the catheter. Alternate designs include a circumferential ring or capillary tube fingers projecting outward. Any surface projection that serves to create additional surface area or any projection that winds and flows into the meatus recesses of the nasal cavity with greater ease will accomplish some aspect of the desired objective.

21 Claims, 15 Drawing Sheets

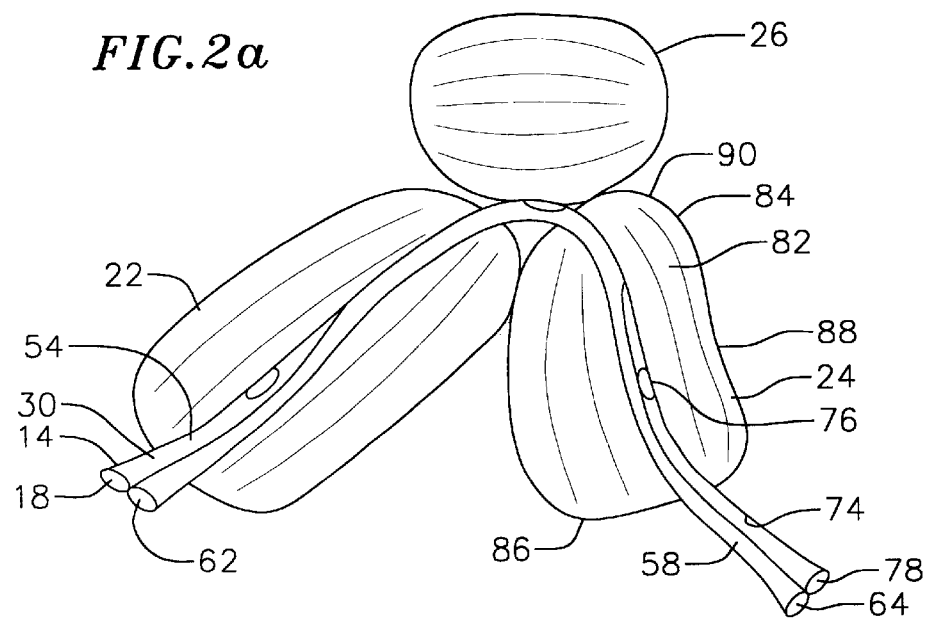
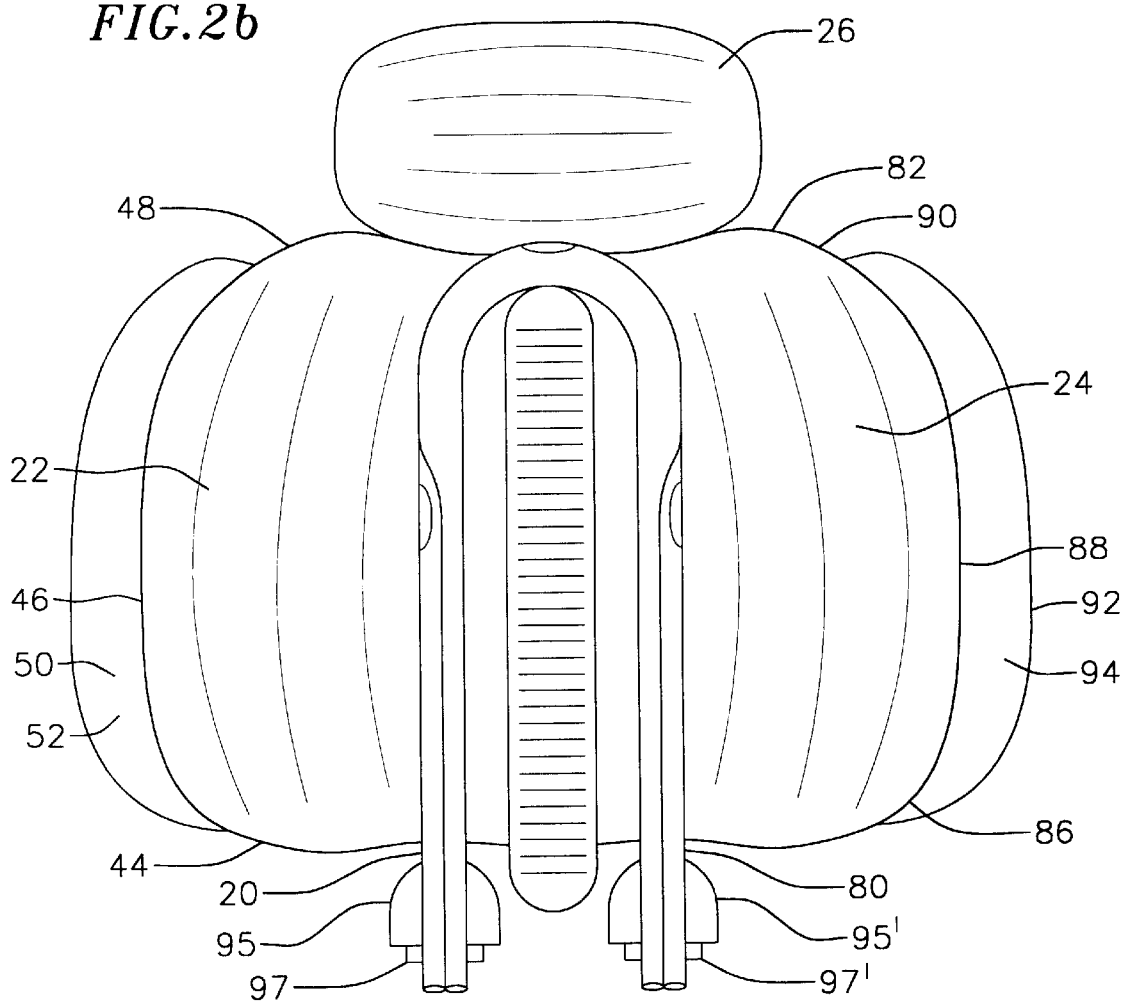

NASAL CATHETER

BACKGROUND

The field of invention relates to medical devices designed to stop serious nosebleeds. There are many products on the market to stop nosebleeds but none of them work much better than putting some type of gauze packing in the nose.

There is a need for a device that will treat the severe nosebleeds or major epistaxsis that is not controlled with gauze slipped into the nose. A device is needed for nosebleeds which are not easily stopped and to replace the one or two inflatable devices, presently available, which are mostly ineffective and tend to be painful.

Part of the difficulty with nosebleeds is that the nasal chamber is not a space with flat walls where pressure can be brought to bare. Instead, the nasal cavity has what can be thought of as serpentine deep grooves, called meatus recesses, in the side walls which are fairly narrow and make it difficult to produce pressure in these recessed areas. The present devices will not easily flow into these recesses to stop a nosebleed. A new device is required that will stop nosebleeds, which do not respond to simpler methods.

Another problem must be solved when designing a device to stop the more serious nosebleed. The nasal cavity is divided by a center wall, the nasal septum, which produces right and left nasal chamber airways. This center wall extends from the anterior opening of the nose posteriorly, but eventually ends so the posterior part of the nose is just one chamber. The new invention should be capable of entering both the right and left anterior nasal chamber airways or nasal cavities.

Therefore, the nasal cavity is made up of two divided chambers anteriorly and a common chamber posteriorly. Nosebleeds can occur either in the anterior or posterior cavities. It is relatively common, especially in older people, to be unable to see where the nosebleed is originating, especially when the treating physician is not an ear, nose and throat (ENT) doctor. When a doctor cannot find the source of bleeding, he/she will commonly call the nosebleed a "posterior nose bleed." The nosebleed may be in the anterior ⅔'s of the nose or in one of the recesses or in the posterior ⅓ common chamber of the nose but a persistant nosebleed is still commonly called a "posterior epistaxsis".

There is a need for a device that puts more uniform pressure into the nose. Presently used devices use a balloon to "blow up" in the nose but the balloon does not conform to the interior configuration of the nose. The balloon device attempts to fill the nasal interior with an expanding balloon by forcing more water into the balloon, but the balloon does not expand into the serpentine recesses of the nose. These recesses in the lateral wall of the nose are individually called a meatus. Meatus can be both singular and plural when describing more than one meatus. A meatus is created by an "overhang structure" on the side wall of the nose called a turbinate.

One of the early methods for treatment is for an "anterior" nose bleed, where gauze is placed into either the right or left side of the nose, whichever is bleeding, or at times both sides of the nose. A "posterior" pack can be placed into the nose in addition to the "anterior" gauze packing. A roll of gauze is inserted into the back of the nose and secured to a second roll of gauze at the opening of the nose with a string so the posterior gauze roll will not fall into the throat. This method is now seldom used since the Foley Catheter method was developed.

The Standard Urological Catheter (Foley Catheter) has a balloon that is expanded with water to put pressure in the back of nose, in the common space posterior to the center wall septum. This balloon also allows the physician to insert gauze into the front of the nose with less concern that the packing will fall into the throat and obstruct the airway. The catheter is clamped at the inlet of the nose to keep the balloon from moving backwards into the throat. The balloon of the Foley Catheter produces excessive pressure and pain when inflated in an attempt to fill the posterior cavity of the nose and still does not conform to or fill the entire space.

The XOMED™ Epistat™ (XOMED™ and Epistat™ are trademarks of Xomed Surgical Products Inc.) represents the latest technology used to attempt to stop the persistent nosebleed. The XOMED™ Epistat™ uses a catheter traversing through the right or left chamber of the nose. You could put one in each side of the nose. Two balloons are inflated with water. The larger balloon is meant to put pressure in the anterior nasal cavity that is divided into right and left side. The small balloon is meant to put pressure in the posterior chamber of the nose. This is the common chamber.

The XOMED™ Epistat™ has inflatable balloons where it is difficult to conform to the shapes of the nasal cavities, especially the anterior cavity. The anterior nasal cavity is the hardest to fill with a balloon. The expanding spherical or ovoid balloon will put minimal pressure in the crevices. Likewise, the posterior nasal cavity is not a sphere and the expanding bulb will not conform to the anatomical space.

In an attempt to control the bleeding, the physician will put more and more pressure in the balloons and this causes a significant amount of pain because of the expanding pressure inside the nose. The pain is produced because the balloon is expanded with much more pressure than needed to compress a bleeding vessel. The increased pressure is used to try to drive the balloon into the crevices or serpentine recesses of the nose. These recesses of the nose are the Superior Meatus, Middle Meatus and Inferior Meatus. Regardless of how much pressure is put into the balloon, the balloon will not flow into the crevices of the nose.

The XOMED™ Epistat™ balloon expands producing a round or ovoid configuration while producing significant pressure in a very small area, with significant pain, and does not fill much of the interior space of the nose such as the lateral crevices. There is not very effective filling of the posterior nose by the posterior balloon of the XOMED™ Epistat™. The balloon expands in about a sphere and takes on a modified configuration only when significant pressure is used in the balloon and it still does not fill much of the posterior airway, because the balloon does not match the anatomical configuration of the posterior nose.

The XOMED™ EPISTAT II™ was believed to have been produced in an attempt to stop bleeding without the need for an anterior nasal balloon. The anterior balloon is the balloon that causes most of the pain. The anterior balloon was replaced with a compressed "sponge" which expands when inserted into the nose. Although the EPISTAT II™ is much less painful, it is not very effective in stopping nosebleeds. The compressed sponge often lacks the force of expansion necessary to place sufficient pressure in the nasal cavities and recesses. There is no external force, such as water from a syringe, that drives the surface of the sponge into the recesses. Only the force of the sponge structure attempting to expand itself is available and this force is most often inadequate.

The present state of technology in medical devices for stopping serious nosebleeds is inadequate since the current devices lack the ability to effectively flow into the recesses of the anterior nasal cavity or fill the posterior nasal cavity and use severe pressure with associated intense pain. Therefore, a need exists for a new medical device that will overcome these deficiencies.

SUMMARY OF THE INVENTION

The present invention will effectively flow into the recesses of the nasal cavity without severe pressure and the associated intense pain thus filling the anterior nasal cavity, meatus and posterior nose without causing significant discomfort. The present invention will provide an improvement over existing devices that do not fill the recesses of the nose, do cause significant pain and still do not stop nosebleeds very effectively.

The objectives are achieved through the design of a nasal catheter system to stop a nosebleed coming from one or both of the nasal airways, either right and/or left nasal airways. A version of the device has two inflatable bags, which in the preferred embodiment are not elastic balloons. The anterior bag is much larger in volume than the anterior nasal cavity. The design of the bag is generally cylindrical but has deep ridges projecting outward producing a "pleated" design with ribs running along and parallel to axis of the catheter. Alternate designs include a circumferential ring or capillary tube fingers projecting outward. Any surface projection that serves to create additional surface area or any projection that winds and flows into the recesses with greater ease will accomplish some aspect of the desired objective.

Traditional devices typically are spherical or ovoid shaped balloons that lack the added surface projections to flow and wiggle into the deep crevices without extreme pressure and associated severe pain to the patient. The shape and redundancy of size of the present invention will allow the anterior bag and surface projections to fill the anterior chamber and "flow" into the deep crevices of the nose without the need for excessive pressure and pain. The addition of surface projections to the anterior bag creates a significantly improved flow capability over the traditional spherical or ovoid shaped devices.

The anterior and posterior bags are twisted around the catheter to allow easy insertion into the nose. The posterior bag is constructed to the shape of the posterior nose and is slightly larger than the volume of the posterior nose. However, the posterior bag is not as redundantly oversized as the anterior bag. The posterior bag is not as redundant so that the bag will not extend or drop down into the throat. The anterior bag, which is more oversized, will actually flow into proximal anterior extent of the posterior nasal cavity to fill any space not occupied by the posterior bag.

The anterior and posterior bags will inflate with water or other fluid to a predetermined size and configuration. The posterior bag is not an elastic balloon, in the preferred embodiment. The anterior and posterior bags are made of medical grade silicone in the preferred embodiment.

A two channel catheter protrudes from the nostril to allow the instillation of water into each bag separately. The ends of the two channels protruding from the nose will be gradually flared to a diameter which fits over a standard hospital syringe used for irrigation or administering medication. The ends of the two channels will not have the bulky injection ports as in the XOMED™ Epistat™.

The existing XOMED™ Epistat™ has two injection ports each containing a valve which allows insertion or removal of water from the catheter. The preferred embodiment differs from the XOMED™ Epistat™, with a catheter which contains two lumens so water can be inserted individually into the anterior and posterior bags but does not have any valves. The two lumens are separated into two channels at the inlet of the nose to allow individual filling and clamping. After the device is inserted into the nose, a soft silicone nasal plug will be "snugged" into the nostril after the common catheter has been brought out through the central channel.

The posterior bag will be inflated with water while pulling on the catheter so the posterior bag does not fall down in the throat. Once the posterior balloon is inflated, the channel to the posterior balloon is closed with a small medical clamp as the channel exits the nasal plug. The nasal plug is kept in place and the anterior bag is inflated with water with some "to and fro" and twisting motion of the catheter to allow the redundant anterior bag to flow into the crevices. The nasal plug is kept in place as the anterior bag is filled so that the redundant anterior bag does not extrude out the nostril.

When the anterior bag is filled and the epistaxsis nosebleed is controlled, a slightly larger clamp is placed on the common catheter as both channels exit from the nasal plug. This clamp and nasal plug keeps the entire catheter/bag system from falling into the throat. Since the posterior bag will be larger in diameter than the anterior nasal airway, the posterior bag keeps the catheter/bag system from extruding out the nostril.

One embodiment of the inventive concept consists of one catheter with two anterior bags and one posterior bag. One of the anterior bags fills the right anterior nose and the other anterior bag fills the left anterior nose. The single posterior bag is designed to completely fill the posterior chamber. All bags can be filled individually through a double channel catheter which exits both nostrils. The catheter enters both the right and left airways. It has an anterior bag for both right and left anterior nasal cavities and one posterior bag for the common posterior nasal cavity. The catheter goes around the posterior septum and is secured anteriorly at the nostril with a nasal plug and clamp at both nostrils.

The individual fluid channels to the anterior and posterior bags are filled individually, clamped individually and then both clamped by a single clamp around the common catheter as it exits the nasal plug to produce a completed intra nasal pressure device. The redundancy of size and ridge projections will flow into all areas.

When the bags are filled with water, the entire system is "snugged" with firmness by pulling on the combined dual common catheter while pressing inward on the nasal plug and clamping the dual common catheter with one clamp. The least complex version has one anterior bag, this device would be more effective and more convenient than other devices now available to stop the milder anterior nosebleeds.

The nasal catheter system includes; a catheter having a first anterior fluid channel, a first anterior output opening, a first anterior input port, and a first external section. There is a first anterior bag fixedly attached to the catheter. The first anterior bag has a first anterior chamber, a first outer surface, a first front end, a first middle portion and a first rear end. There is a plurality of first anterior elongated ridges attached to the first outer surface and spanning over about the first middle portion, the plurality of first anterior elongated ridges have a plurality of first anterior ridge cavities. The first anterior ridge cavities are in communication with and connected to the first anterior chamber. The nasal catheter system is inserted into a first anterior nasal cavity and then the catheter is filled with a fluid that flows through the first anterior fluid channel and into the first anterior bag, thereby expanding the first anterior bag and producing pressure upon the first anterior nasal cavity.

The nasal catheter system can additionally include a posterior fluid channel that has a posterior section, a first posterior input port and a posterior output opening. Attached to the catheter is a posterior bag with a posterior chamber. The nasal catheter system is inserted into the first anterior nasal cavity and a posterior nasal cavity so that when the posterior fluid channel is filled with a fluid, the fluid flows through the posterior fluid channel and into the posterior bag, thereby expanding the posterior bag and producing pressure upon the posterior nasal cavity.

The nasal catheter system can also be expanded to include a second anterior bag attached to a second anterior fluid channel having a second anterior output opening, a second anterior input port and a second external section. The second anterior bag has a second anterior chamber, a second outer surface, a second front end, a second middle portion and a second rear end. There is a plurality of second anterior elongated ridges attached to the second outer surface and spanning over about the second middle portion. The plurality of second anterior elongated ridges have a plurality of second anterior ridge cavities that are in communication with and connected to the second anterior chamber. The nasal catheter system may be additionally inserted into a second anterior nasal cavity and when the catheter is filled with a fluid, the fluid flows through the second anterior fluid channel and into the second anterior bag, thereby expanding the second anterior bag and producing pressure upon the second anterior nasal cavity.

The nasal catheter system can have an elongated section removably attached to the first external section or the second external section of the catheter. The elongated section may be inserted through the first anterior nasal cavity, the posterior nasal cavity and into the throat. Then a secondary member can be inserted through the second anterior nasal cavity, the posterior nasal cavity and into the throat. The secondary member is then attached to the elongated section of the catheter. Next the secondary member is pulled back through the second anterior nasal cavity, pulling the catheter, the posterior bag, the first anterior bag and the second anterior bag into the posterior nasal cavity, first anterior nasal cavity and second anterior nasal cavity.

A second posterior input port can be added to the posterior fluid channel. This allows filling of the posterior bag from either the first or second posterior input port. The first anterior bag, second anterior bag and posterior bag are made of silicone in one embodiment.

The surface projections may be arranged in a variety of configurations, including where the plurality of first anterior elongated ridges span from about the first front end to about the first rear end including the first middle portion and the plurality of second anterior elongated ridge span from about the second front end to about the second rear end including the second middle portion.

Another version has the first anterior bag with a first anterior chamber, a first long axis with a plurality of first anterior circumferencial ridges attached to a first outer surface and axially positioned in circumferencial rings about the first long axis. The plurality of first anterior circumferencial ridges span over about the first middle portion. The plurality of first anterior circumferencial ridges have a plurality of first anterior circumferencial ridge cavities. The first anterior circumferencial ridge cavities are in communication with the first anterior chamber.

The second anterior bag would have a similar arrangement with a second anterior chamber, a second long axis, a second outer surface, a second front end, a second middle portion and a second rear end. A plurality of second anterior circumferencial ridges are attached to the second outer surface and axially positioned in circumferencial rings about the second long axis. The plurality of second anterior circumferencial ridges span over about the second middle portion, the plurality of second anterior circumferencial ridges having a plurality of second anterior circumferencial ridge cavities that are in communication with the second anterior chamber.

Another version of the surface projections from the first anterior bag is a plurality of first anterior capillary tubes with a first open end and a first closed end. The plurality of first anterior capillary tubes are attached to the first outer surface and take the form of finger-like projections extending generally perpendicular from the first outer surface and spanning over about the first middle portion. The plurality of first anterior capillary tubes have a plurality of first anterior capillary tube cavities. The first open end of the first anterior capillary tube cavities are in communication with the first anterior chamber.

In a similar arrangement the second anterior bag can have a plurality of second anterior capillary tubes. The second anterior bag has a second anterior chamber, a second outer surface, a second front end, a second middle portion and a second rear end. The plurality of second anterior capillary tubes have a second open end, a second closed end and are attached to the second outer surface. The plurality of second anterior capillary tubes take the form of finger-like projections extending generally perpendicular from the second outer surface and spanning over about the second middle portion, the plurality of second anterior capillary tubes having a plurality of second anterior capillary tube cavities where the second open end of the second anterior capillary tube cavities are in communication with the second anterior chamber.

Another alternative arrangement of the nasal catheter system is where the plurality of first anterior capillary tubes span from about the first front end to about the first rear end including the first middle portion and the plurality of second anterior capillary tubes span from about the second front end to about the second rear end including the second middle portion.

BRIEF DESCRIPTION OF THE DRAWINGS

FIG. 2a shows a top view.

FIG. 2b shows a top view of the system with nasal plugs and clamps.

DESCRIPTION

Figure 1A:
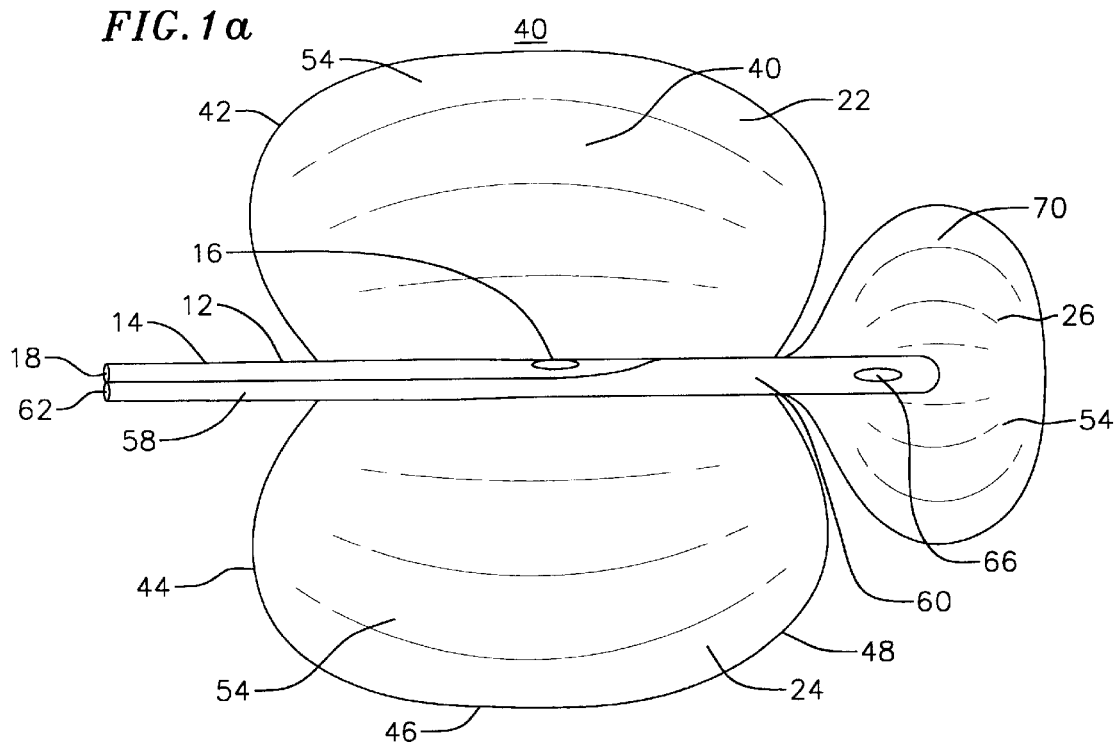
FIG. 1a shows a top view of the invention.

Referring to FIGS. 1–16, A nasal catheter system 10 includes a catheter 12 having a first anterior fluid channel 14, a first anterior output opening 16, a first anterior input port 18, and a first external section 20. The first anterior bag 22 is securely attached to the catheter 12. This simplest version with one first anterior bag 22 is illustrated in FIG. 14. The nasal catheter system 10 can be more complex and have a second anterior bag 24 and a posterior bag 26 attached to the catheter 12 as shown in FIGS. 1, 2a, 2b.

The nasal catheter system 10 is inserted into a first anterior nasal cavity 32 and when the catheter 10 is filled with a fluid 30 via the first anterior input port 18, the fluid 30 flows through the first anterior fluid channel 14 and into the first anterior bag 22, thereby expanding the first anterior bag 22 and producing pressure upon the first anterior nasal cavity 32. The first anterior fluid channel 14 ends at about the first anterior output opening 16.

Figure 4:
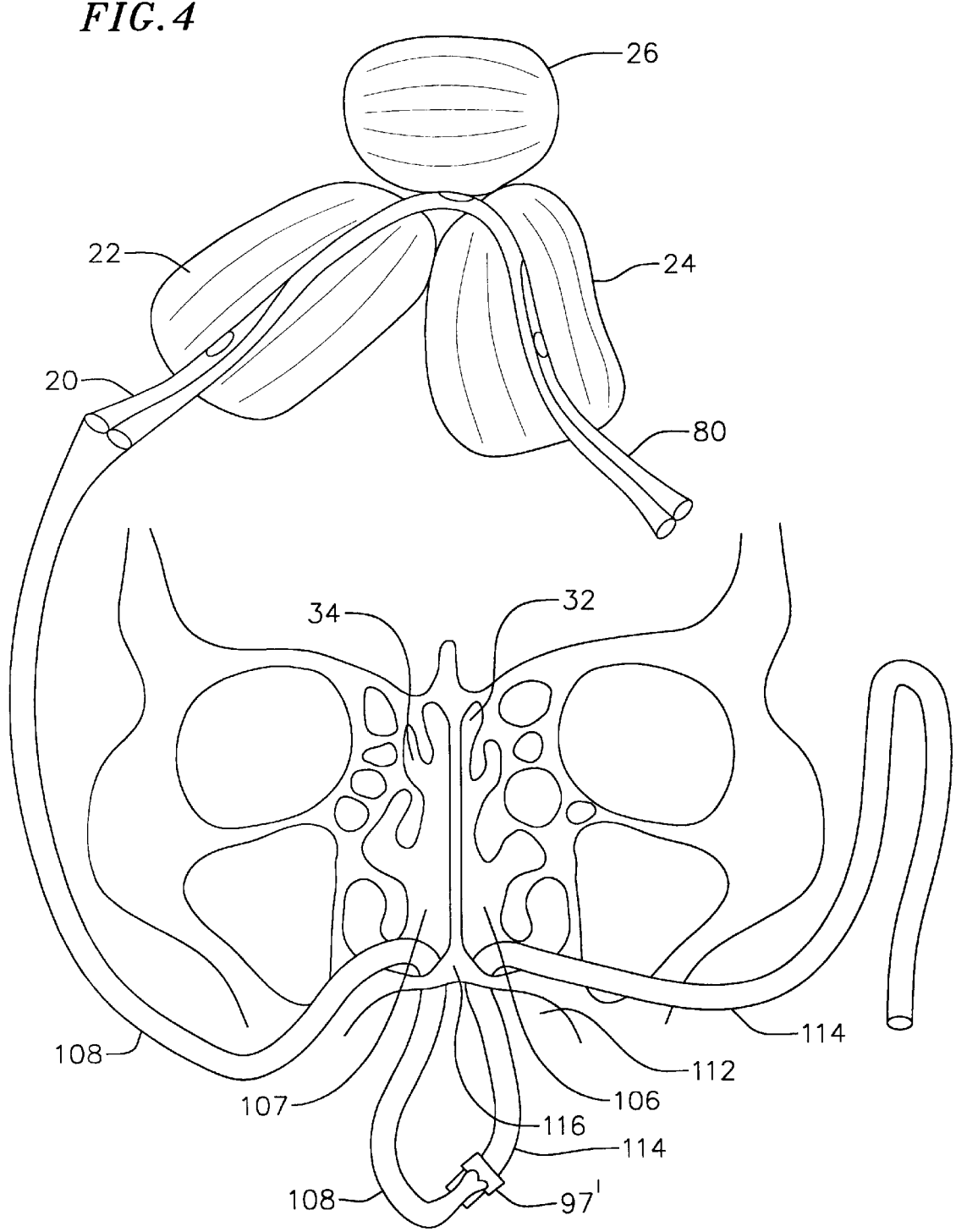
FIG. 4 shows a top view of the catheter with the secondary member added and a cutaway frontal view of the nasal cavities.

When included a second anterior bag 24 is inserted into the second anterior nasal cavity 34 and the first anterior bag 22 is inserted into a first anterior nasal cavity 32, as shown on FIGS. 4, 5. The posterior bag 26 is inserted into the posterior nasal cavity 36 that is behind the first and second anterior nasal cavity 32, 34.

The first anterior bag 22 has a first anterior chamber 40, a first outer surface 42, a first front end 44, a first middle portion 46 and a first rear end 48. A plurality of first anterior elongated ridges 50 are attached to the first outer surface 42 and span over about the first middle portion 46. The plurality of first anterior elongated ridges 50 have a plurality of first anterior ridge cavities 52. The first anterior ridge cavities 52 are connected to and in communication with the first anterior chamber 40.

The preferred fluid 30 is water 54. When water 54 is injected into the first anterior fluid channel 14 it passed through the first anterior output opening 16 into the first anterior ridge cavities 52 and the first anterior chamber 40. The water 54 creates pressure upon the first anterior ridge cavities 52 and the first anterior chamber 40 causing them to expand and producing pressure upon the first anterior nasal cavity 32.

When the posterior bag 26 is included then the catheter 10 has a posterior fluid channel 58 that has a posterior section 60, a first posterior input port 62 and a posterior output opening 66. A second posterior input port 64 can be added, in which case, the posterior fluid channel 58 would be extended and the second posterior input port 64 attached to the posterior fluid channel 58. Both the first posterior input port 62 and second posterior input 64 port provide fluid 30 or water 54 to the posterior output opening 66. Either the first posterior input port 62 or second posterior input port 64 can be used for convenience.

The posterior bag 26 is attached to the catheter 10 near the posterior output opening 66. The posterior bag 26 is filled when water 54 or fluid 30 is inserted into the first posterior input port 62 or the second posterior input port 64 and the water 54 flows though the posterior fluid channel 58 and through the posterior output opening 66 into the posterior bag 26. The posterior fluid channel 58 generally parallels and adjoins the first anterior fluid channel 14 and the second anterior fluid channel 74. The posterior bag 26 has a posterior chamber 70 that fills with water 54 and expands the posterior bag 26 and produces pressure upon the posterior nasal cavity 36.

In some patients the physician cannot ascertain from which anterior nasal cavity 32, 34 the bleeding is occurring. The solution is to provide a second anterior bag 24 attached to the catheter 12. Filling of the second anterior bag 24 is accomplished by adding to the catheter 12; a second anterior fluid channel 74 having a second anterior output opening 76, a second anterior input port 78, and a second external section 80.

Figure 14A:
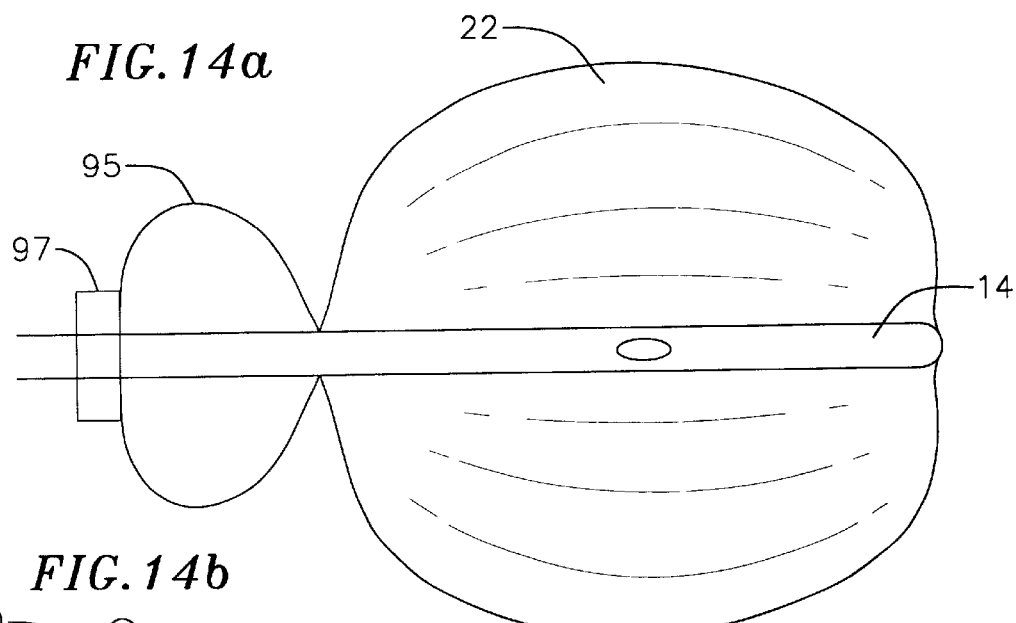
FIG. 14a is a top view of an anterior bag, plug and clamp.
Figure 14B:
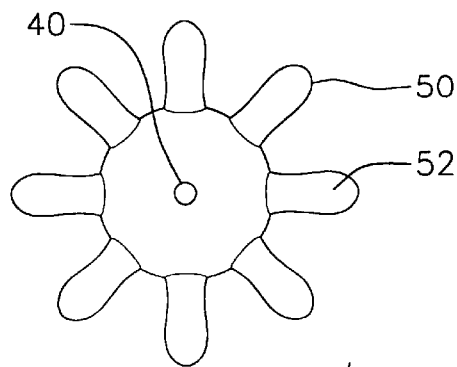
FIG. 14b is an end view showing the elongated ridges.
Figure 14C:
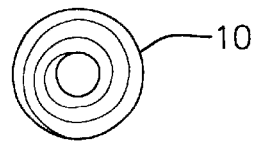
FIG. 14c shows an end view of the invention wrapped prior to insertion into the nasal cavity.
Figure 14D:
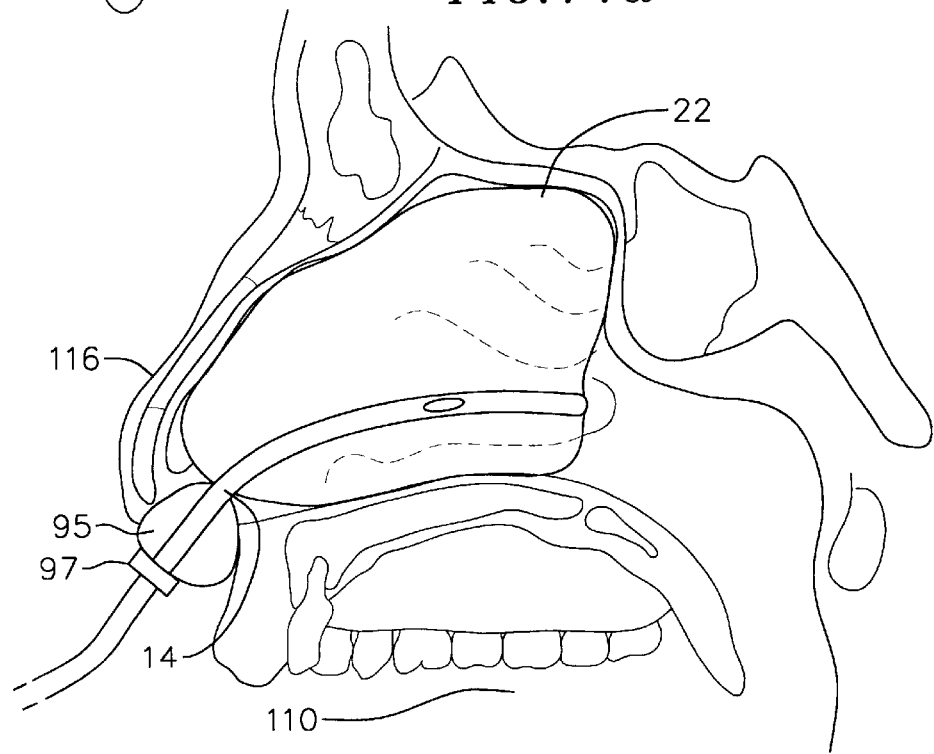
FIG. 14d shows a side view of the anterior bag inserted into the nasal cavity.

Referring particularly to FIGS. 2a, 2b; the second anterior bag 24 is attached to the second anterior fluid channel 74, the second anterior bag has a second anterior chamber 82, a second outer surface 84, a second front end 86, a second middle portion 88 and a second rear end 90. Attached to the second outer surface 84 are a plurality of second anterior elongated ridges 92 that span over about the second middle portion 88. The plurality of second anterior elongated ridges 92 have a plurality of second anterior ridge cavities 94. The second anterior ridge cavities 94 are connected to and are in communication with the second anterior chamber 82. FIG. 1c and FIG. 14c show the nasal catheter system 10 being coiled or wrapped for insertion.

The second anterior bag 24 may be inserted into a second anterior nasal cavity 34 and when the catheter 12 is filled with a fluid 30, the fluid 30 flows through the second anterior fluid channel 74 and into the second anterior bag 24, which expands the second anterior bag 24 and producing pressure upon the second anterior nasal cavity 32.

Referring to FIG. 2b, to secure the nasal catheter system 10 within the nasal cavity 28 a nasal plug 95 is used to receive the first external section 20 and a second nasal plug 95' secures the second external section 80. The first external section 20 can then be clamped by a clamping device 97 and the second external section 80 is secured by clamping device 97', thus securing the nasal catheter system 10 within the nasal cavity 28.

Pressure is placed upon the meatus recesses 96 of the nasal cavity 28 when the nasal catheter system 10 is inserted into a nasal cavity 28 and a fluid 30 is inserted into the first anterior input port 18 of the catheter 12, and the fluid 30 passes through the catheter 12 and passes through the first anterior output opening 16 into the first anterior bag 22. This expands the first anterior chamber 22 and the plurality of first anterior ridge cavities 52. The expansion causes the plurality of first anterior ridge cavities 52 to press against the interior walls of the nasal cavity 28 and flow into additional open spaces of the meatus recesses 96. Since the first anterior ridge cavities 52 will search for a path of least resistance, the first anterior ridge cavities 52 will wind and flow into the meatus recesses 96 thereby producing pressure upon the nasal cavity 28 and meatus recesses 96 that is much more effective and less painful than conventional methods.

Figure 5A:
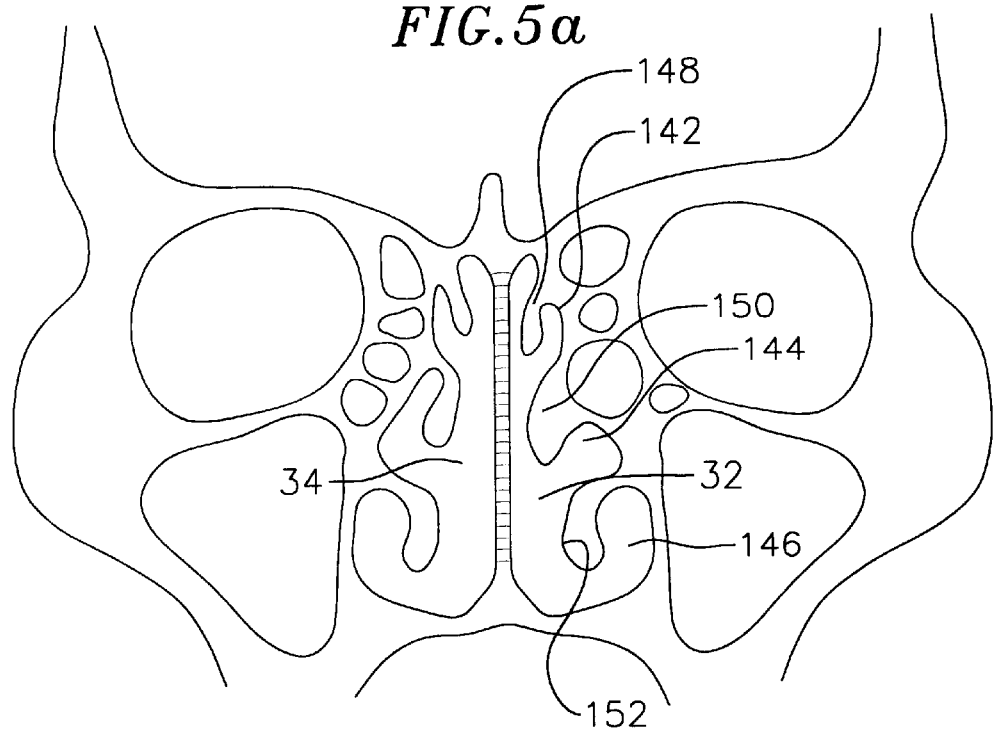
FIG. 5a shows a cutaway frontal view of the nasal cavities.
Figure 10A:
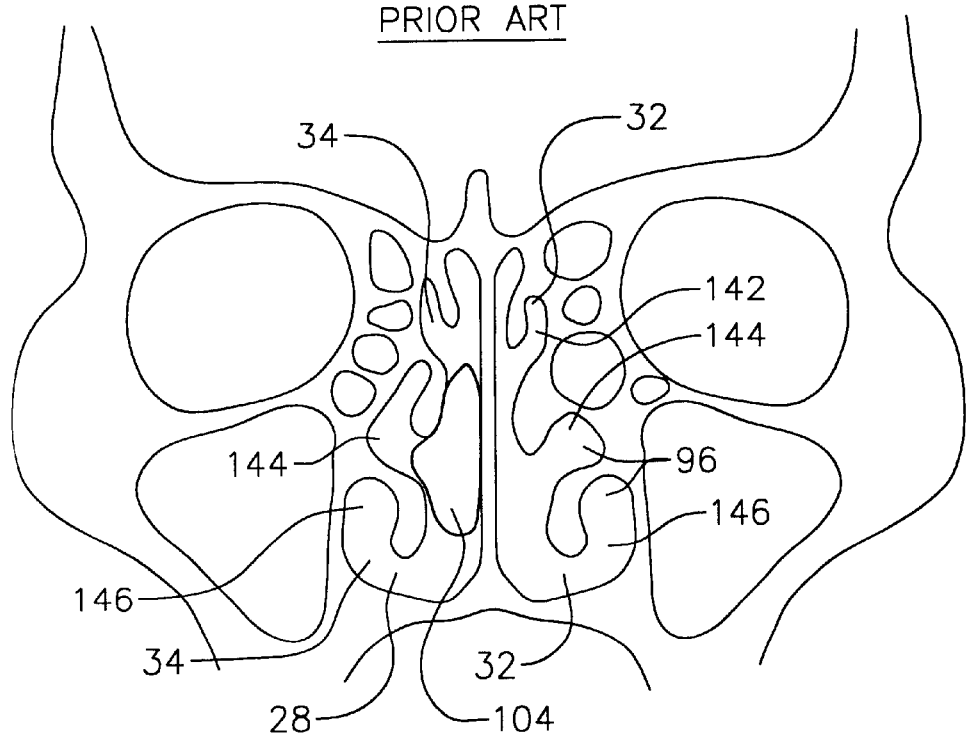
FIG. 10a shows a frontal view of incomplete filling of the anterior nasal cavity by the prior art.

FIG. 5a, 10a illustrates the meatus recesses 96. They are the superior meatus 142, middle meatus 144 and inferior meatus 146. The meatus recesses 142, 144, 146 are deep and winding recesses that are not easily accessed by traditional round or ovoid inflatable balloons 104.

Figure 3:
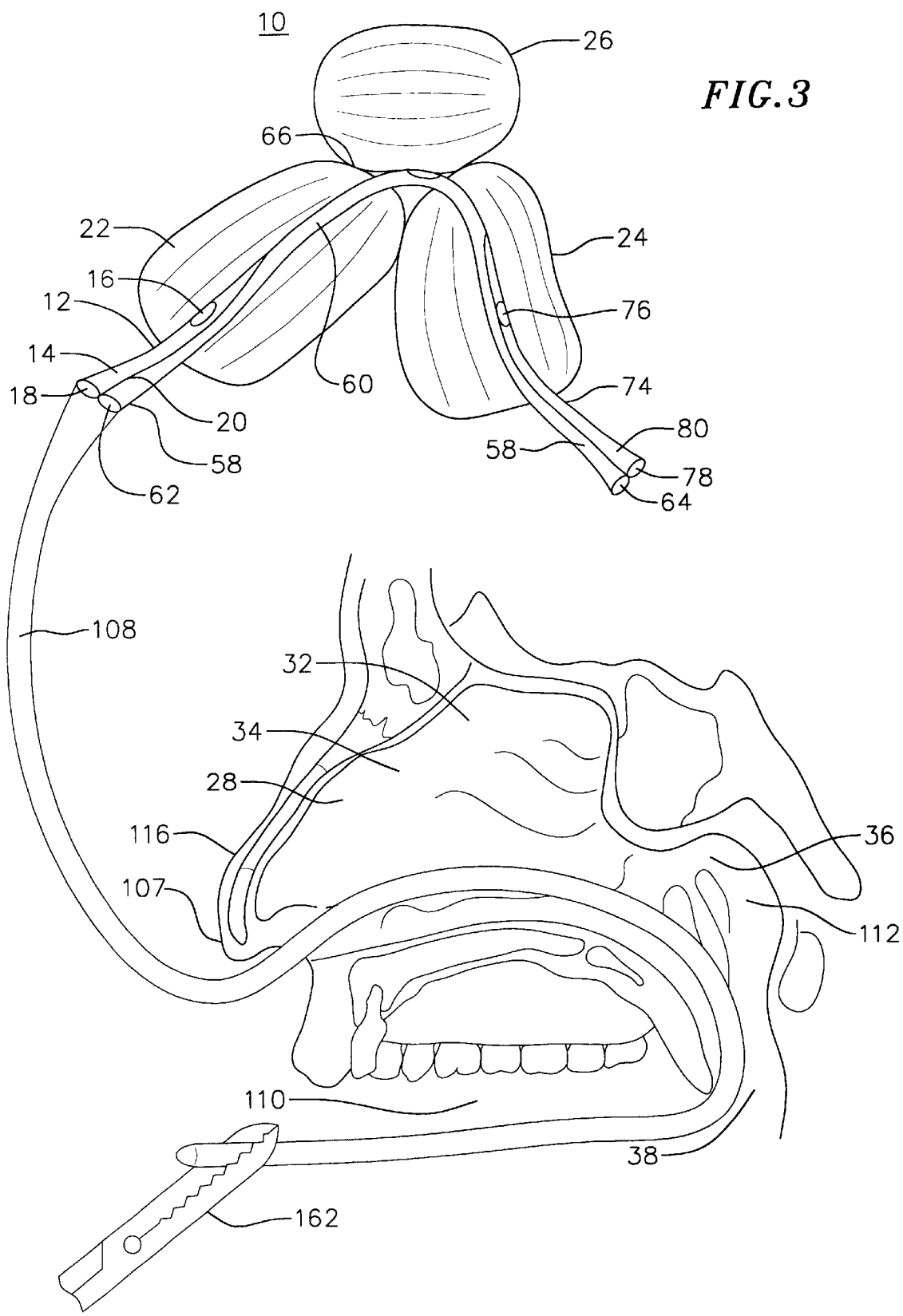
FIG. 3 shows a top view of the system with an elongated section.

Referring to FIG. 3 and FIG. 4, the insertion of the three-bag embodiment into the nose 116 requires more than just pushing it into either or both nostrils 106, 107. When the second anterior bag 24 is included it is necessary to pull the first anterior bag 22 and catheter 12 through the second anterior nasal cavity 34, the posterior nasal cavity 36 and into the throat 38 in order to reach the first anterior nasal cavity 32. The catheter system 10 must be inserted into the second nostril 107 on one side of the nose 116 and advanced into the posterior nasal cavity 36 and then brought into the opposite first posterior nasal airway 112 and out through the first anterior nasal cavity 32 and first nostril 106. To accomplish this the leading end, external section, of the device's catheter 12 is elongated by eighteen to twenty-four inches which allows the insertion of the elongated section 108 of the catheter 12 into the second nostril 107. The elongated section 108 is brought out the mouth by advancing the catheter 12 through the nose 116 until it can be visualized looking through the mouth 110 into the throat 38 and grasped with a hemostat 162 to pull it from the throat 38 and out of the mouth 110.

Although the maneuver as depicted on FIG. 3 puts the catheter system 10 into the second nostril 107 and brings it out the mouth 110, it does not result in the catheter 12 being brought out the other first posterior nasal airway 112. To do this a second and separate tube depicted as secondary member 114 needs to be inserted into the opposite first nostril 106 and advanced into the back of the throat 38 and pulled from the throat 38 and out the mouth 110. This secondary member 114 does not have any inflatable bag. The secondary member 114 can be a second catheter. Its only purpose is to attach to the elongated portion 108 of the catheter 12 and pull the catheter system 10 from the back of the throat 38 into the first posterior nasal airway 112 of the opposite side of the nose 116 and out through the first anterior nasal cavity 32 and first nostril 106.

FIG. 4 illustrates how the secondary member 114 is inserted into the second nostril 107, is brought through the mouth 110 and attaches to the elongated section 108 of the catheter 12 with a small circular clamp device 97'. A circular clamp device 97' or other commonly used clamping medical device can be used to attach the secondary member 114 to the elongated portion 108 of the catheter 12. The catheter 12 is then pulled into the nose 116 by pulling the secondary member 114 which pulls the catheter 12 into the second nostril 107, then to the back of the nose 116 and then forward into the opposite first anterior nasal cavity 32 and out through the opposite first nostril 106. The elongated section 108 is discarded by cutting the catheter 12 as it exits from the first nostril 106 of the nose 116. The three bags 22, 24, 26 are inflated with water 54 and secured at the nostrils 106, 107 by clamping the common catheter 12 over the nasal plugs 95.

The catheter 12 is depicted with an elongated section 108 where the secondary member 114 is used to pull the nasal catheter system 10 through the nasal cavity 28 when a second anterior bag 24 is used. In a variation the secondary member 114 can be attached directly to a lengthened first external section 20 or second external section 80 of the catheter 12, depending on the design. The secondary member 114 is cut and discarded once the procedure is complete.

The catheter 12 is inserted through the second anterior nasal cavity 34, the posterior nasal cavity 36 and into the throat 38 where the secondary member 114 is then attached. The secondary member 114 may be inserted through the first anterior nasal cavity 32, the posterior nasal cavity and into the throat 38. The secondary member 114 is then attached to the elongated section 108 of the catheter 12. The secondary member 114 is pulled back through the first anterior nasal cavity 32, pulling the catheter 12, the posterior bag 26, the first anterior bag 22 and the second anterior bag 24 into the posterior nasal cavity 36, first anterior nasal cavity 32, and second anterior nasal cavity 34.

Although not illustrated, rather than using the three bag nasal catheter system 10 that requires pulling portions of the nasal catheter system 10 through the throat 38; an alternative is to use an embodiment where two nasal catheter system 10 are used that consist of a catheter 12 with a first anterior bag 22 and a posterior bag 26, with a second nasal catheter system 10 consisting of just a second anterior bag 24 and separate catheter 12. The two systems 10 are not connected so they can be inserted separately into the first anterior nasal cavity 32 and the second anterior nasal cavity 34.

This alleviates the need to pull the first anterior bag 22 all the way through the second anterior nasal cavity 34 and the posterior cavity 36, in order to reach the first anterior nasal cavity 32. The advantage of the three bag nasal catheter system 10 is that once inserted into the nasal cavity 28 the posterior bag 26, the first anterior bag 22 and the second anterior bag 24 are all connected and serve to hold each other firmly and securely into proper position.

The nasal catheter system 10 can be constructed of various materials. Materials commonly used in the medical industry for catheter 12 are acceptable. In the preferred embodiment the first anterior bag 22, second anterior bag 24 and posterior bag are made of medical grade silicone with the appropriate expandability for accessing the meatus recesses 96 and providing adequate pressure to stop the nose bleed.

Figure 1B:
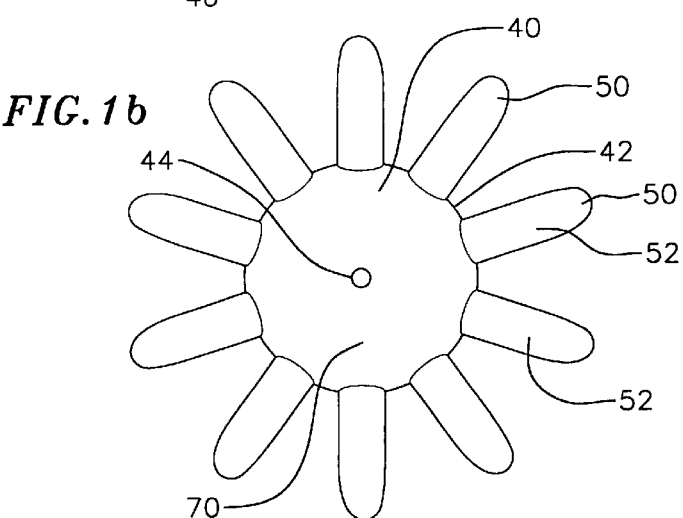
FIG. 1b shows an end view illustrating the ribbed ridges.
Figure 1C:
FIG. 1c is an end view of the invention wrapped about the catheter.
Figure 1D:
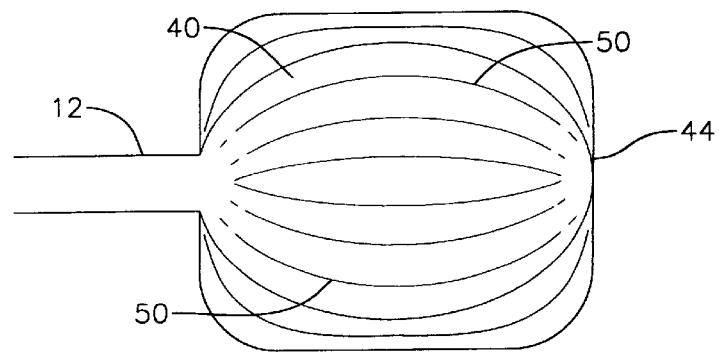
FIG. 1d shows a lateral side view illustrating the ribbed ridges.

Referring to FIGS. 1b, 2b; surface projections attach to the first and second anterior bag 22, 24. The surface projections may vary in configuration. An effective design of the surface projections is with a plurality of first anterior elongated ridges 50 and second anterior elongated ridges 92 that are capable of effectively accessing the meatus recesses 96 without creating painful pressure within the nasal cavity 28. The plurality of first anterior elongated ridges 50 span from about the first front end 44 to about the first rear end 48 including the first middle portion 46 of the first anterior bag 22. The plurality of second anterior elongated ridges 92 span from about the second front end 86 to about the second rear end 90 including the second middle portion 88 of the second anterior bag 24.

When the catheter 12 is filled with a fluid 30, the fluid 30 flows through the first anterior fluid channel 14 and into the first anterior bag 22, thereby expanding the first anterior bag 22 and first anterior elongated ridge cavities 52 producing pressure upon the first anterior nasal cavity 32.

The plurality of first anterior elongated ridges 50 shown in FIGS. 1b, 2b and second anterior elongated ridges 92 may vary in placement quantity, circumference, shape, length and other characteristics. Other variations of the surface projections include circumferencial ridges 118, 122 shown in FIG. 15a–c and capillary tubes 128, 138 shown in FIG. 16a–c that also may vary in placement quantity, circumference, shape, length and other characteristics.

Figure 15A:
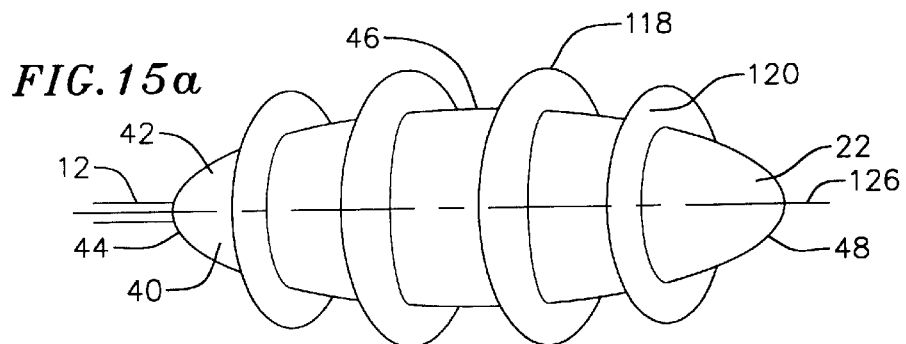
FIG. 15a is a top perspective view of the circumferential rings.
Figure 15B:
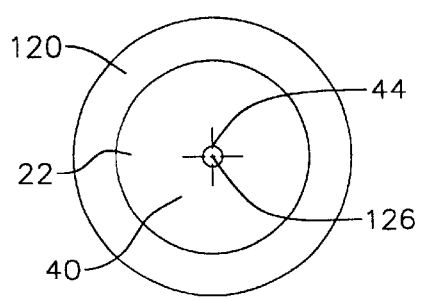
FIG. 15b shows an end view of the first anterior circumferential rings.

FIG. 15a, 15b illustrates the plurality of first anterior circumferencial ridge 118 attached to the first outer surface 42 and axially positioned in circumferencial rings about the first long axis 126 and spanning over about the first middle portion 46. The plurality of first anterior circumferencial ridge 118 have a plurality of first anterior circumferencial ridge cavities 120. The first anterior circumferencial ridge cavities 120 are in communication with the first anterior chamber 40.

Figure 15C:
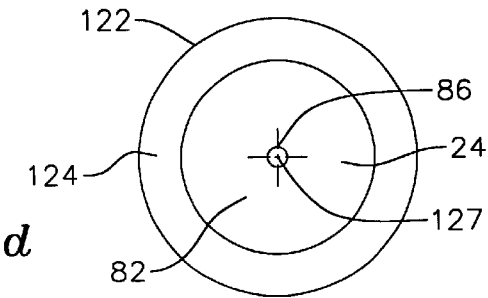
FIG. 15c shows an end view of the second anterior circumferential rings.
Figure 15D:
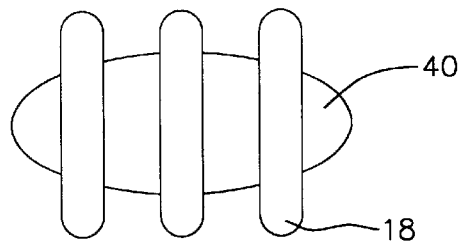
FIG. 15d shows a side view of the second anterior circumferential rings.

In a similar arrangement, the second anterior bag 24 includes a plurality of second anterior circumferencial ridges 122 attached to the second outer surface 84 and axially positioned in circumferencial rings about the second long axis 127. The plurality of second anterior circumferencial ridges 122 span over about the second middle portion 89. FIG. 15c shows the plurality of second anterior circumferencial ridges 122 having a plurality of second anterior circumferencial ridge cavities 124, the second anterior circumferencial ridge cavities 124 are in communication with the second anterior chamber 82. The first anterior circumferencial ridges 118 and second anterior circumferencial ridges 122 are similar in most all characteristics and function, other than which anterior bag 22, 24 they are associated with.

Figure 16A:
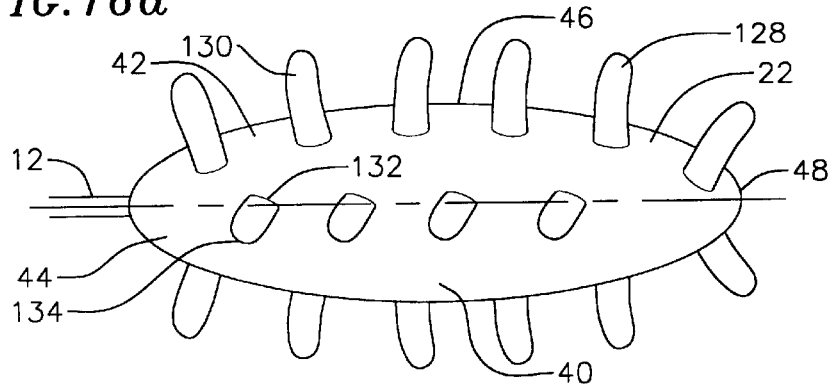
FIG. 16a is a top perspective view of the capillary tubes.
Figure 16B:
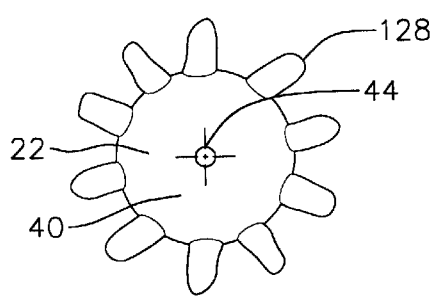
FIG. 16b shows an end view of the first anterior capillary tubes.
Figure 16C:
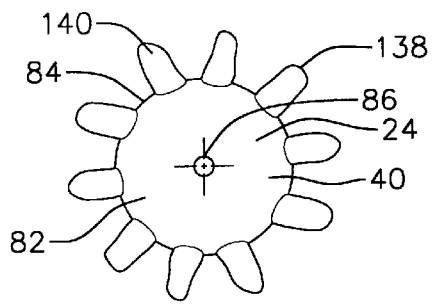
FIG. 16c shows an end view of the second anterior capillary tubes.

FIGS. 16a, 16b, 16c show another variation of the surface projections is a plurality of first anterior capillary tubes 128. The first anterior bag 22 includes a plurality of first anterior capillary tubes 128 attached to the first outer surface 42 having a first open end 132 and a first closed end 134 and attached to the first outer surface 42. The first anterior capillary tubes 128 take the form of finger-like projections extending generally perpendicular from the first outer surface 42 and spanning over about the first middle portion 46. The plurality of first anterior capillary tubes 128 having a plurality of first anterior capillary tube cavities 130. The first open end 132 of the first anterior capillary tube cavities 130 are in communication with the first anterior chamber 40.

As shown in FIG. 16c; in a similar arrangement, the second anterior bag 24 includes a plurality of second anterior capillary tubes 138 attached to the second outer surface 84. The plurality of second anterior capillary tubes 138 have a plurality of second anterior capillary tube cavities 140 that are in communication with the second anterior chamber 82. The first anterior capillary tubes 128 and second anterior capillary tubes 138 are similar in most all characteristics and function, other than which anterior bag 22, 24 they are associated with.

FIG. 16a shows the plurality of first anterior capillary tubes 128 spanning from about the first front end 44 to about the first rear end 48 including the first middle portion 46. The plurality of second anterior capillary tubes 138 span from about the second front end 86 to about the second rear end 90 including the second middle portion 88.

Parts of the nasal catheter system 10 can be manufactured from medical grade silicone, rubber or any other sufficiently expandable materials that are safe for usage internally within the patient.

Figure 5B:
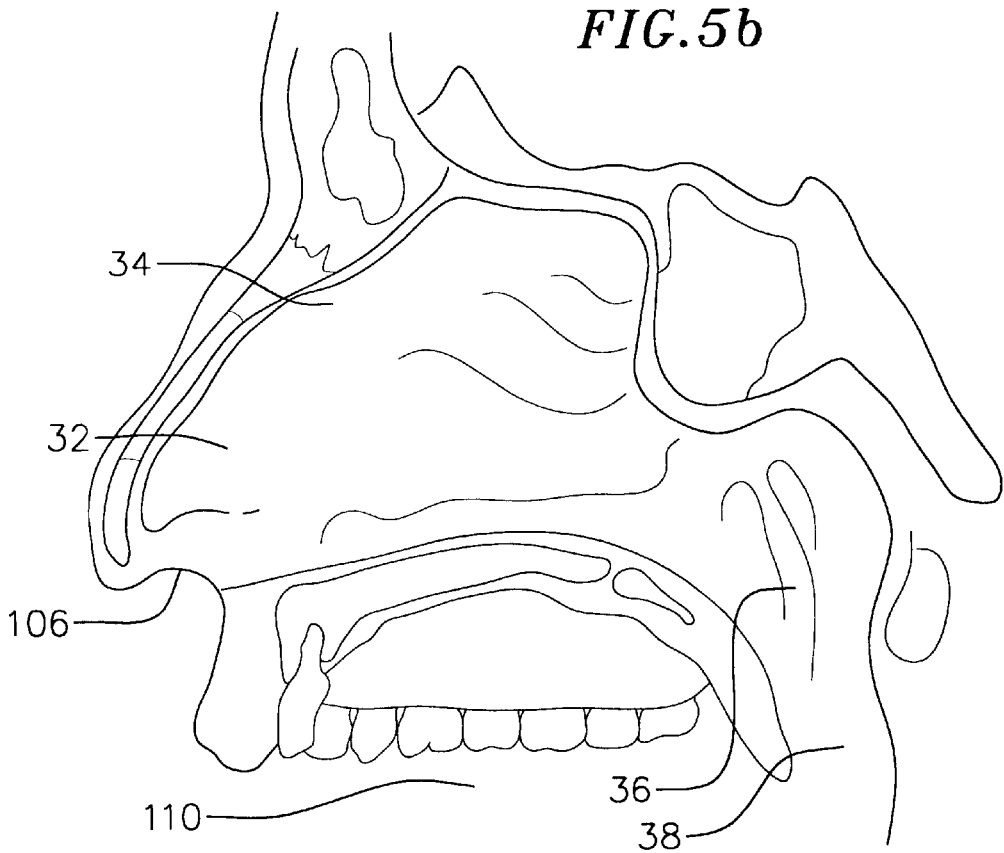
FIG. 5b shows cutaway a side view of the nasal cavities.
Figure 6:
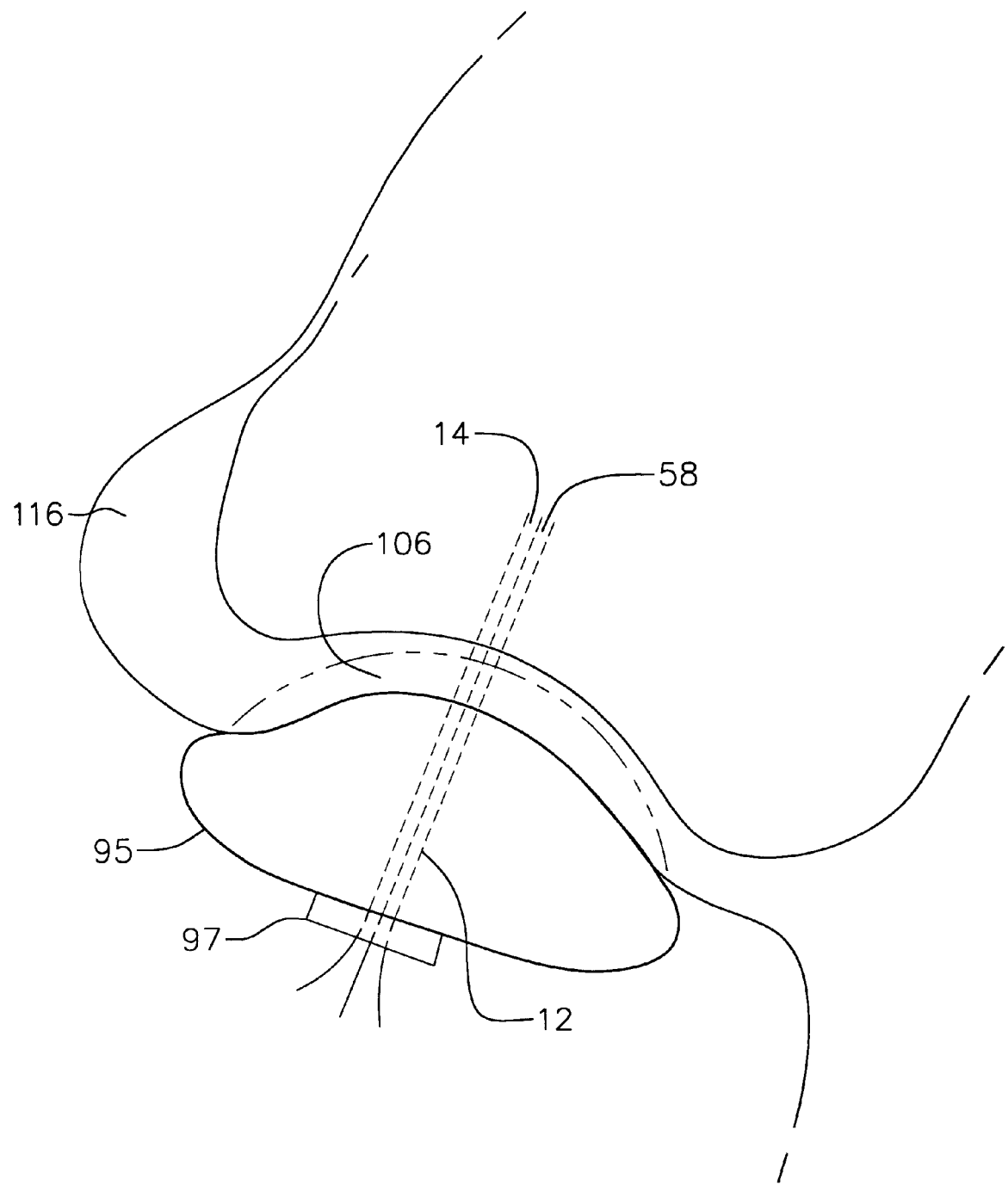
FIG. 6 shows a side view of the nasal cavities snugged with a nasal plug and clamp.

FIG. 5a shows the difficult to access crevices of the nasal cavity 28. These crevices are the Superior Meatus 142, Middle Meatus 144 and Inferior Meatus 146, which are separated by the Superior Turbinate 148, Middle Turbinate 150 and Inferior Turbinate 152. The nasal septum 154 separates the first anterior nasal cavity 32 from the second anterior nasal cavity 32. FIG. 5b shows the first anterior nasal cavity 32 and posterior nasal cavity 36.

Figure 7A:
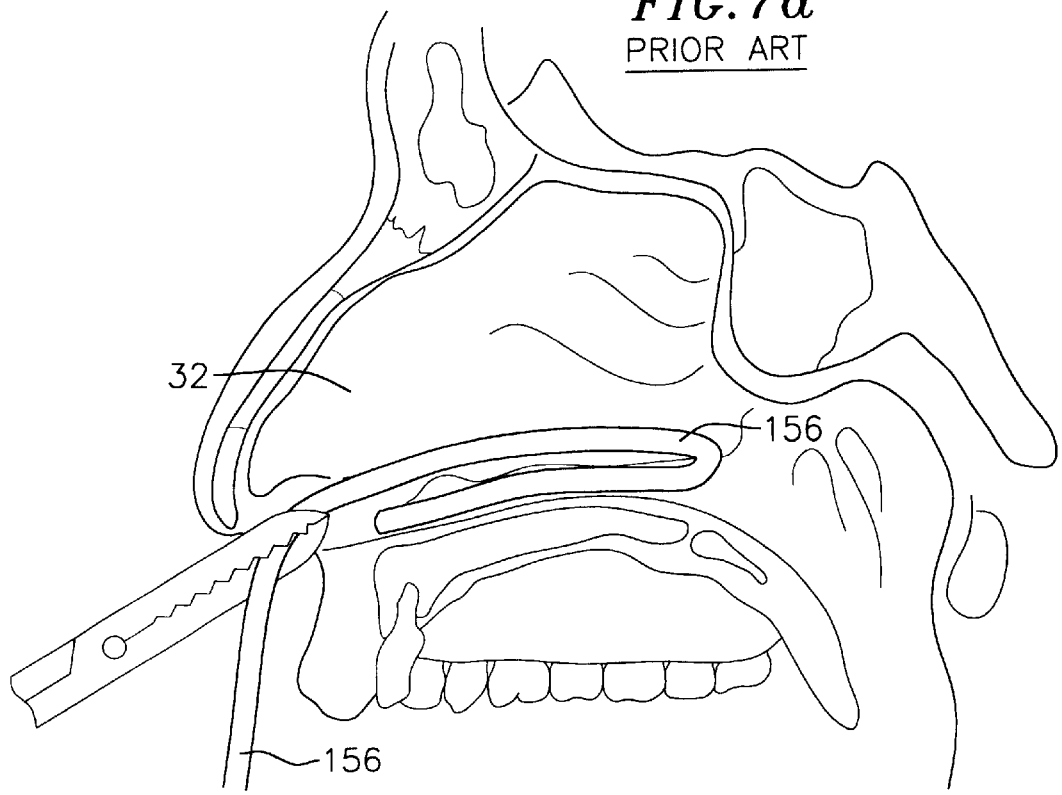
FIGS. 7a, 7b and 7c show prior art methods with gauze.
Figure 7B:
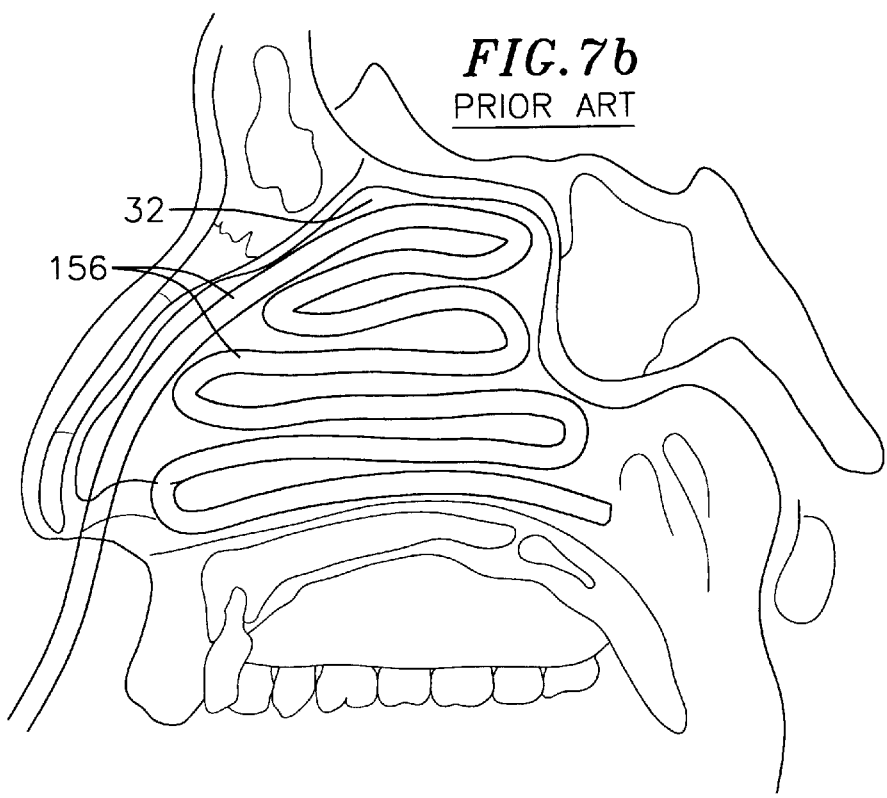
Figure 7C:
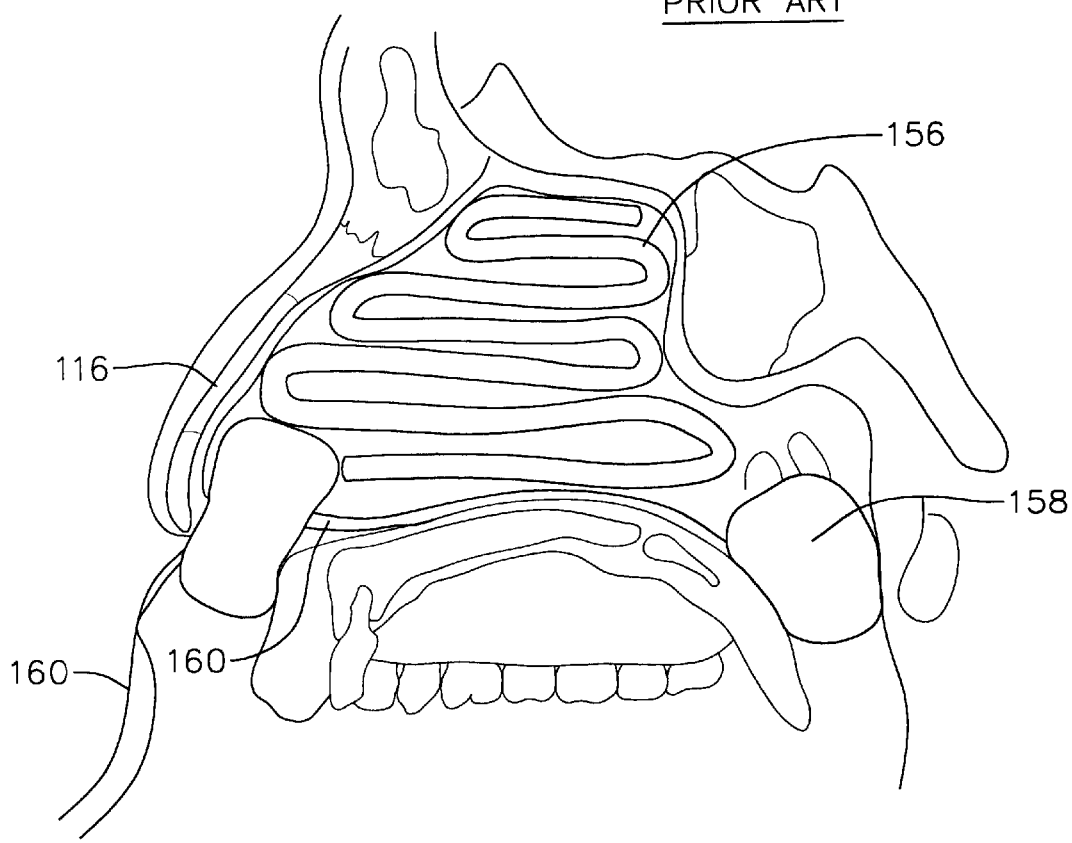

FIGS. 7a, 7b, 7c illustrates the prior art method of gauze 156 being placed into the nose. FIGS. 7a and 7b show the anterior gauze 156 is packed into the anterior nasal cavity 32, 34. FIG. 7c shows one of the early methods for treatment for an "anterior" nose bleed, where gauze is placed into either the right or left side of the nose, whichever is bleeding or at times both sides of the nose. A "posterior" gauze pack 158 is placed into the nose 116 in addition to the "anterior" gauze packing 156. A roll of gauze is inserted into the back of the nose and secured to a second roll of gauze at the opening of the nose 116 with a string 160 so the posterior gauze roll 158 will not fall into the throat. This method is now seldom used since the Foley Catheter method was developed.

Figure 8:
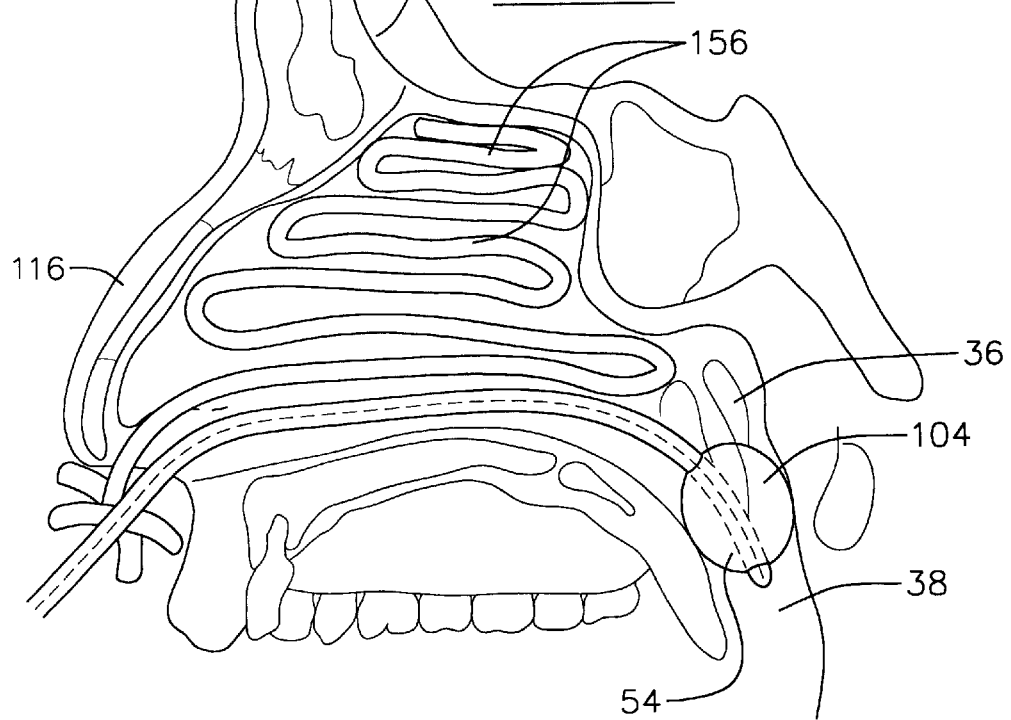
FIG. 8 shows a prior art method with gauze and a posterior round or ovoid balloon.

FIG. 8 shows the Standard Urological Catheter (Foley Catheter) with a balloon 104 that is expanded with water 54 to put pressure in the back of nose, in the common space posterior nasal cavity 36 to the center wall (septum). This balloon 104 also allows the physician to insert gauze into the front of the nose 116 with less concern that the packing will "fall" into the throat 38 and obstruct the airway. The catheter 12 is clamped at the inlet of the nose to keep the balloon 104 from moving backwards into the throat 38. The balloon 104 of the Foley Catheter produces excessive pressure and pain when inflated in an attempt to fill the posterior nasal cavity 36.

Figure 9:
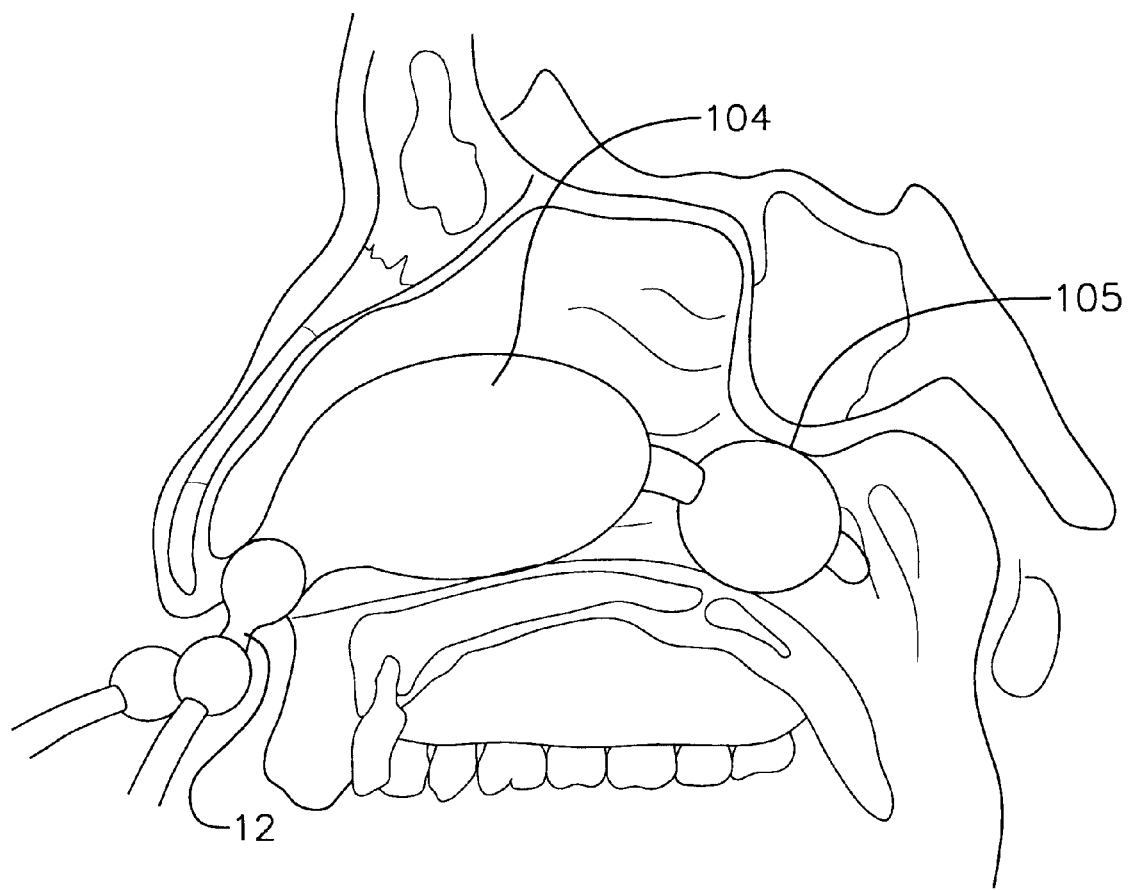
FIG. 9 shows a prior art method with an anterior round or ovoid balloon and posterior ovoid balloon.

FIG. 9 shows the Xomed™ Epistat™, which represents the latest technology used to attempt to stop the persistent nosebleed. The Xomed™ Epistat™ uses a catheter 12 traversing through the right or left chamber of the nose. You could put one in each side of the nose. Two balloons 104, 105 are inflated with water. The larger balloon 104 is meant to put pressure in the anterior nasal cavity which is divided into right and left side. The small balloon 105 is meant to put pressure in the posterior nasal cavity 36 of the nose 116, this is the common chamber.

Figure 11A:
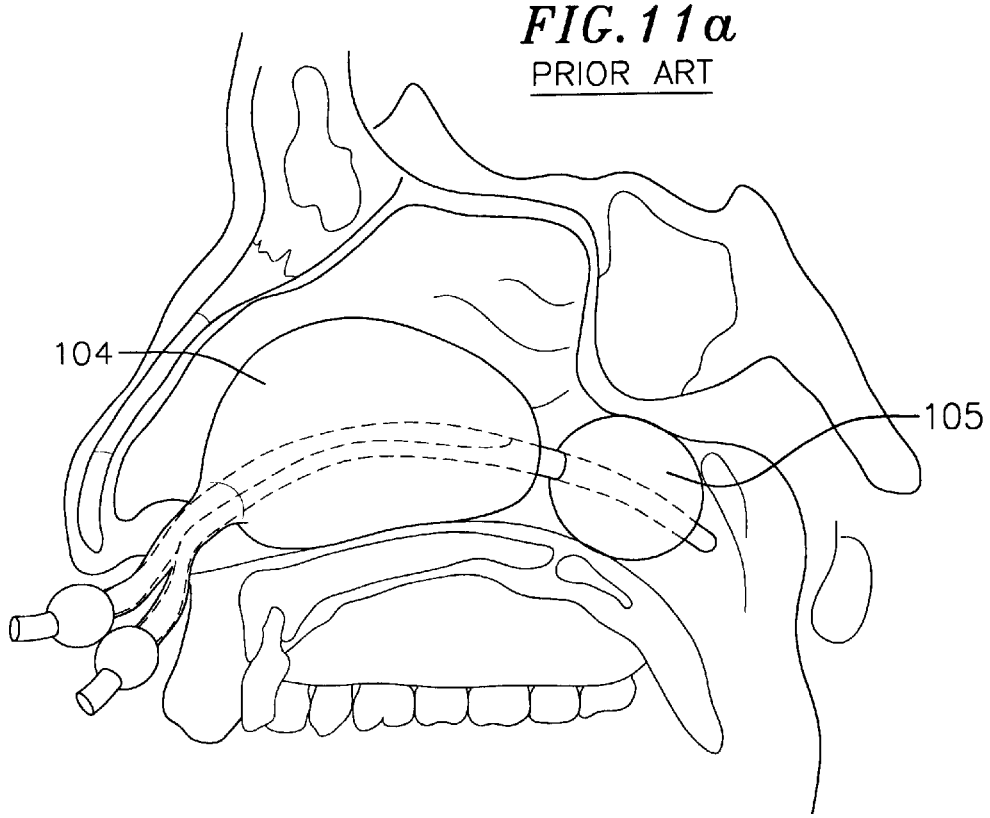
FIG. 11a shows a side view of incomplete filling of the nasal cavity by the prior art.

As shown in FIG. 10a and FIG. 11a the Xomed™ Epistat™ has inflatable balloons 104, 105 which can never conform to the shapes of the nasal cavities 28, especially the anterior nasal cavity 32, 34. The anterior nasal cavity 32, 34 is the hardest to fill with a balloon 104. The expanding spherical or ovoid balloon 104 will put minimal pressure in the crevices of the meatus recesses 96. Likewise, the posterior nasal cavity 36 is not a sphere and the expanding bulb will not conform to the anatomical space.

In an attempt to control the bleeding, the physician will put more and more pressure in the balloons 104, 105 and this causes a significant amount of pain because of the expanding pressure inside the nose 116. The pain is produced because the balloon 104 is expanded with much more pressure than needed to compress a bleeding vessel. The increased pressure is used to try to "drive" the balloon into the crevices or "serpentine meatus recesses" 96 of the nose 116. Regardless of how much pressure is put into the balloon, the balloon will not "flow" into the crevices of the nose.

FIGS. 10a and 11a show how the Xomed™ Epistat™ balloon 104 expands producing a round or ovoid configuration while producing significant pressure in a very small area, with significant pain, and not filling any of the major area of the nose such as the Superior Meatus 142, Middle Meatus 144 and Inferior Meatus 146 crevices. There is ineffective filling of the posterior nasal cavity 36 by the posterior balloon of the Xomed™ Epistat™. The balloon can only expand in a sphere and takes on a modified configuration only with significant pressure in the balloon and still does not fill the posterior nasal cavity 36.

Figure 10B:
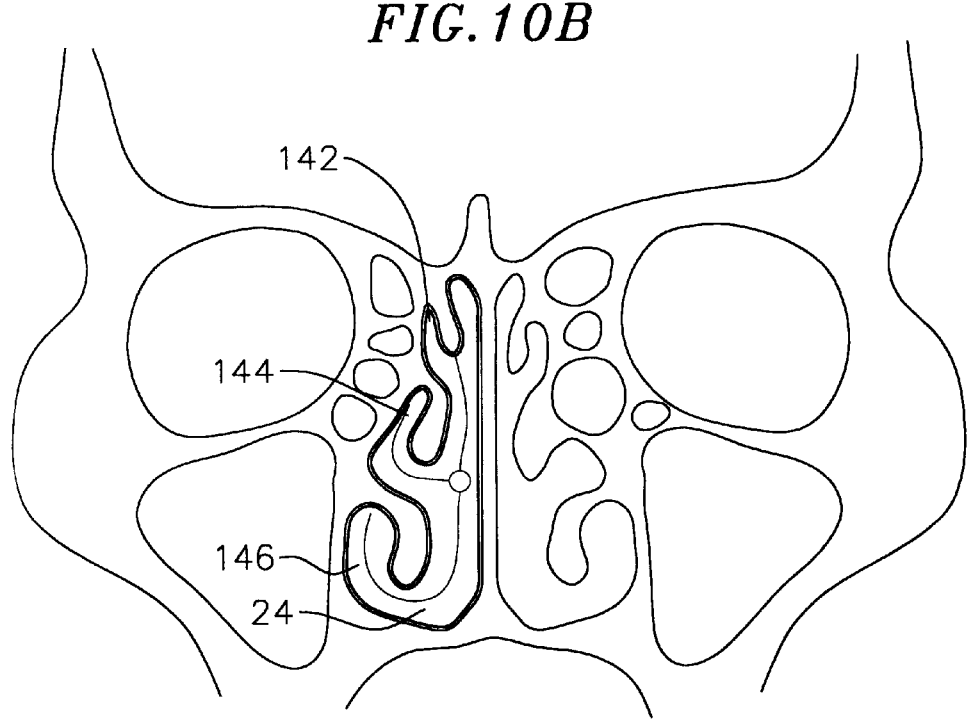
FIG. 10b shows a frontal view of complete filling of the anterior nasal cavity by the present invention.
Figure 11B:
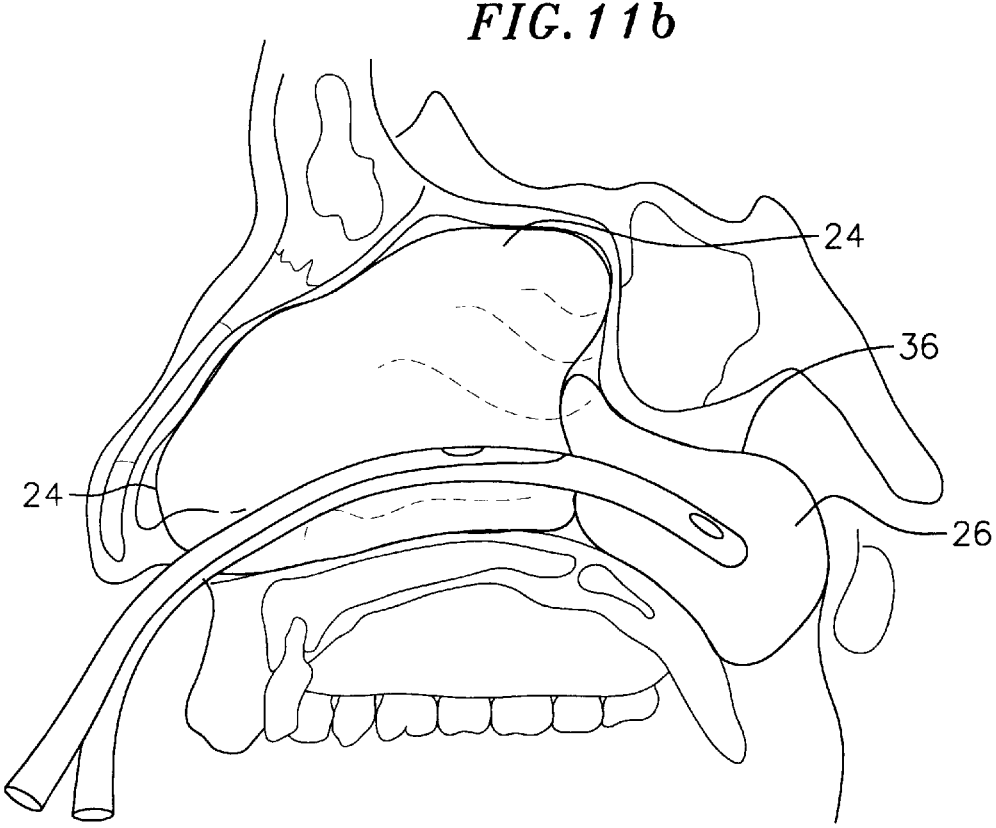
FIG. 11b shows a side view of complete filling of the posterior nasal cavity by the present invention.

FIGS. 10b and 11b show complete filling of the Superior Meatus 142, Middle Meatus 144 and Inferior Meatus 146 by the second anterior bag 24 of the present invention. The posterior bag 26 is designed to the shape of the anatomical space in the posterior cavity 36. It is slightly larger than this space to effect pressure in all areas and completely fills the posterior nasal cavity 36.

FIG. 12a, 12b, 13a and 13b show the catheter 10 with the first anterior fluid channel 14 to the first anterior bag 22 and posterior fluid channel 58 to the posterior bag 26 that allows them to be filled individually, clamped individually and then both clamped by a single clamp 97 around the common catheter 12 as it exits the nasal plug 95 to produce a completed intra nasal catheter system 10.

Figure 12A:
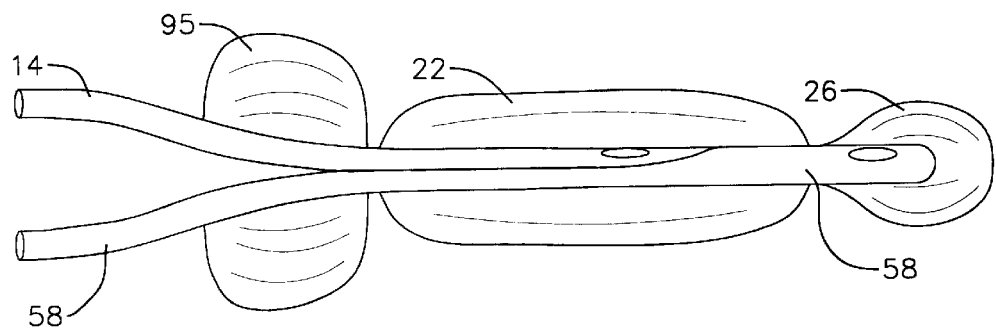
FIG. 12a, 12b, 13a, 13b illustrate top views of the steps of filling the anterior and posterior bags that are then clamped.
Figure 12B:
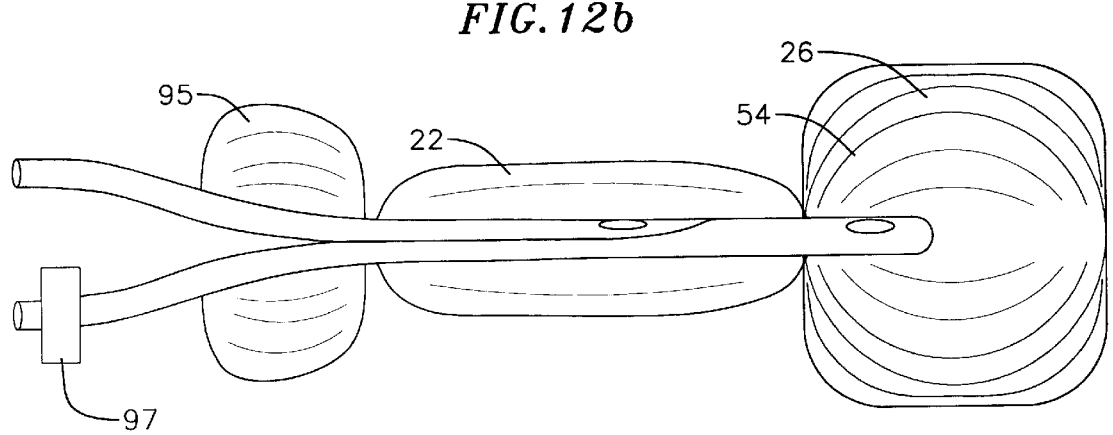
Figure 13A:
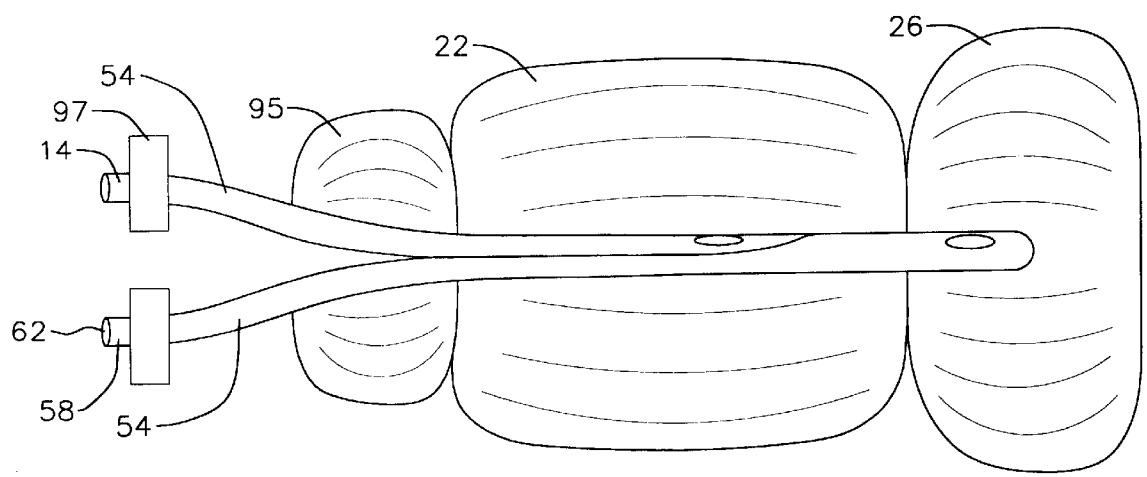
Figure 13B:
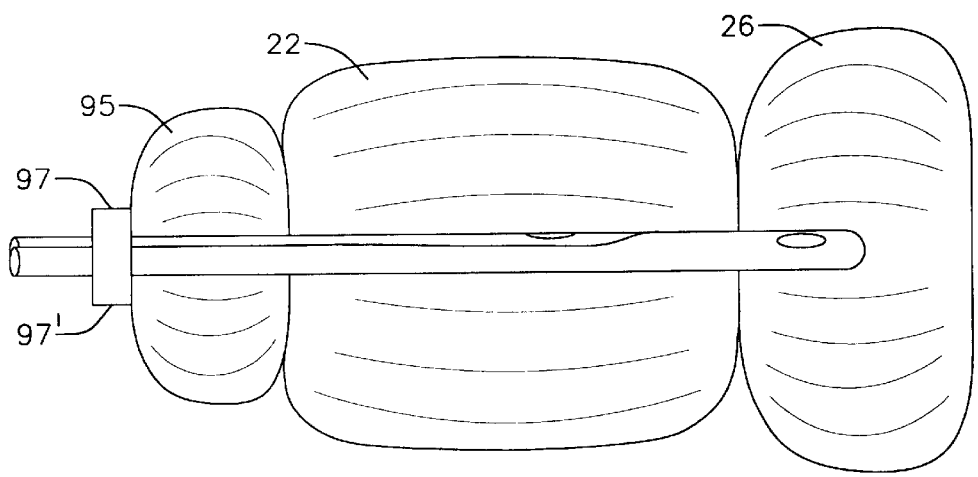

FIG. 12b shows the posterior bag 26 filed with water 54 and the posterior fluid channel 58 to the posterior bag 26 individually clamped. FIG. 13a show both the posterior bag 26 and first anterior bag 22 filled with water 54. The posterior fluid channel 58 and anterior fluid channel 14 are then individually sealed with clamps 97, 97'. The redundancy of size and ridge projections will flow into all areas FIG. 13b illustrates both bags 26, 22 filled with water and the entire system "snugged" with firmness by pulling on the combined dual common catheter 10 while pressing inward on the nasal plug 95 and clamping the dual common catheter 10 with one clamp 97.

Filling the variation with three bags 22, 24, 26 would be carried out in a similar manner once the nasal catheter system 10 was in place inside the nose 116. The posterior bag 26 would be filled from the left nostril through the first posterior input port 62 while the second posterior input port 64 to the posterior bag 26 is individually clamped. The first and second anterior bags 22, 24 would then be filled and individually clamped. A common clamp 97 would then be applied to the common catheter 10 coming out each nostril and through the nasal plug 95.

The least complex version has one first anterior bag 22, this device would be more effective and more convenient than other devices now available to stop the milder anterior nosebleeds.

Although the present invention has been described in considerable detail with regard to the preferred versions thereof, other versions are possible. Therefore, the appended claims should not be limited to the descriptions of the preferred versions contained herein.

What is claimed is:

1. A nasal catheter system comprising:
    a) a catheter having a first anterior fluid channel, a first anterior output opening, a first anterior input port, and a first external section; and
    b) a first anterior bag fixedly attached to the catheter, the first anterior bag having a first anterior chamber, a first outer surface, a first front end, a first middle portion and a first rear end, and a plurality of first anterior elongated ridges attached to the first outer surface and spanning over about the first middle portion, the plurality of first anterior elongated ridges having a plurality of first anterior ridge cavities, wherein the first anterior ridge cavities are in communication with the first anterior chamber;
        whereby the nasal catheter system may be inserted into a first anterior nasal cavity and when the catheter is filled with a fluid, the fluid flows through the first anterior fluid channel and into the first anterior bag, thereby expanding the first anterior bag and producing pressure upon the first anterior nasal cavity.

2. The nasal catheter system of claim 1, wherein the catheter further comprises of:
    a) a posterior fluid channel having a posterior section, a first posterior input port and a posterior output opening; and
    b) a posterior bag attached to the catheter, the posterior bag having a posterior chamber, whereby the nasal catheter system may be inserted into the first anterior nasal cavity and a posterior nasal cavity so that when the posterior fluid channel is filled with a fluid, the fluid flows through the posterior fluid channel and into the posterior bag, thereby expanding the posterior bag and producing pressure upon the posterior nasal cavity.

3. The nasal catheter system of claim 2, wherein the catheter further comprises:
    b) a second anterior fluid channel having a second anterior output opening, a second anterior input port, and a second external section; and
    c) a second anterior bag attached to the second anterior fluid channel, the second anterior bag having a second anterior chamber, a second outer surface, a second front end, a second middle portion and a second rear end, and a plurality of second anterior elongated ridges attached to the second outer surface and spanning over about the second middle portion, the plurality of second anterior elongated ridges having a plurality of second anterior ridge cavities, wherein the second anterior ridge cavities are in communication with the second anterior chamber;
        whereby the nasal catheter system may be additionally inserted into a second anterior nasal cavity and when the catheter is filled with a fluid, the fluid flows through the second anterior fluid channel and into the second anterior bag, thereby expanding the second anterior bag and producing pressure upon the second anterior nasal cavity.

4. The nasal catheter system of claim 3 wherein the catheter further comprises of an elongated section removably attached to the first external section or the second external section of the catheter;
    wherein the elongated section may be inserted through the second anterior nasal cavity, the posterior nasal cavity and into the throat whereby a secondary member can be inserted through the first anterior nasal cavity, the posterior nasal cavity and into the throat, wherein the secondary member can be attached to the elongated section of the catheter, so that the secondary member is pulled back through the first anterior nasal cavity, pulling the catheter, the posterior bag, the first anterior bag and the second anterior bag into the posterior nasal cavity, first anterior nasal cavity and second anterior nasal cavity.

5. The nasal catheter system of claim 4, wherein the posterior fluid channel has a second posterior input port.

6. The nasal catheter system of claim 5, wherein the first anterior bag, second anterior bag and posterior bag are made of silicone.

7. The nasal catheter system of claim 6 wherein the plurality of first anterior elongated ridges span from about the first front end to about the first rear end including the first middle portion and the plurality of second anterior elongated ridge span from about the second front end to about the second rear end including the second middle portion.

8. A nasal catheter system comprising:
   a) a catheter having a first anterior fluid channel, a first anterior output opening, an first anterior input port, and a first external section; and
   b) a first anterior bag fixedly attached to the catheter, the first anterior bag having a first anterior chamber, a first long axis, a first outer surface, a first front end, a first middle portion and a first rear end; and
      a plurality of first anterior circumferencial ridges attached to the first outer surface and axially positioned in circumferencial rings about the first long axis and spanning over about the first middle portion, the plurality of first anterior circumferencial ridges having a plurality of first anterior circumferencial ridge cavities, wherein the first anterior circumferencial ridge cavities are in communication with the first anterior chamber;
   whereby the nasal catheter system may be inserted into a first anterior nasal cavity and when the catheter is filled with a fluid, the fluid flows through the first anterior fluid channel and into the first anterior bag, thereby expanding the first anterior bag and producing pressure upon the first anterior nasal cavity.

9. The nasal catheter system of claim 8, wherein the catheter further comprises of:
   a) a posterior fluid channel having a posterior section, a first posterior input port and a posterior output opening; and
   b) a posterior bag attached to the catheter, the posterior bag having a posterior chamber, whereby the nasal catheter system may be inserted into a first anterior nasal cavity and posterior nasal cavity and when the posterior fluid channel is filled with a fluid, the fluid flows through the posterior fluid channel and into the posterior bag, thereby expanding the posterior bag and producing pressure upon the posterior nasal cavity.

10. The nasal catheter system of claim 9, wherein the catheter further comprises:
   a) a second anterior fluid channel having a second anterior output opening, a second anterior input port, and a second external section; and
   b) a second anterior bag attached to the second anterior fluid channel, the second anterior bag having a second anterior chamber, a second long axis, a second outer surface, a second front end, a second middle portion and a second rear end; and
      a plurality of second anterior circumferencial ridges attached to the second outer surface and axially positioned in circumferencial rings about the second long axis and spanning over about the second middle portion, the plurality of second anterior circumferencial ridges having a plurality of second anterior circumferencial ridge cavities, wherein the second anterior circumferencial ridge cavities are in communication with the second anterior chamber;
   whereby the nasal catheter system may be inserted into a second anterior nasal cavity and when the catheter is filled with a fluid, the fluid flows through the second anterior fluid channel and into the second anterior bag, thereby expanding the second anterior bag and producing pressure upon the second anterior nasal cavity.

11. The nasal catheter system of claim 10 wherein the catheter further comprises of:
   a) an elongated section;
      wherein the elongated section may be inserted through the second anterior nasal cavity, the posterior nasal cavity and into the throat whereby a secondary member can be inserted through the first anterior nasal cavity, the posterior nasal cavity and into the throat, wherein the secondary member can be attached to the elongated section of the catheter, so that the secondary member is pulled back through the first anterior nasal cavity, pulling the catheter, the posterior bag, the first anterior bag and the second anterior bag into the posterior nasal cavity, first anterior nasal cavity and second anterior nasal cavity.

12. The nasal catheter system of claim 11, wherein the posterior fluid channel has a second posterior input port.

13. The nasal catheter system of claim 12, wherein the first anterior bag, second anterior bag and posterior bag are made of silicone.

14. The nasal catheter system of claim 13 wherein the plurality of first anterior circumferencial ridges span from about the first front end to about the first rear end including the first middle portion and the plurality of second anterior circumferencial ridges span from about the second front end to about the second rear end including the second middle portion.

15. A nasal catheter system comprising:
   a) a catheter having a first anterior fluid channel, a first anterior output opening, a first anterior input port, and a first external section; and
   b) a first anterior bag fixedly attached to the first catheter, the first anterior bag having a first anterior chamber, a first outer surface, a first front end, a first middle portion and a first rear end;
      and a plurality of first anterior capillary tubes having a first open end and a first closed end and attached to the first outer surface, taking the form of finger-like projections extending generally perpendicular from the first outer surface and spanning over about the first middle portion, the plurality of first anterior capillary tubes having a plurality of first anterior capillary tube cavities, wherein the first open end of the first anterior capillary tube cavities are in communication with the first anterior chamber;
   whereby the nasal catheter system may be inserted into a first anterior nasal cavity and when the first catheter is filled with a fluid, the fluid flows through the first anterior fluid channel and into the first anterior bag, thereby expanding the first anterior bag and producing pressure upon the first anterior nasal cavity.

16. The nasal catheter system of claim 15, wherein the catheter further comprises of:
   d) a posterior fluid channel having a posterior section, a first posterior input port and a posterior output opening; and
   b) a posterior bag attached to the catheter, the posterior bag having a posterior chamber, whereby the nasal catheter system may be inserted into a nasal cavity and posterior nasal cavity and when the posterior fluid channel is filled with a fluid, the fluid flows through the posterior fluid channel and into the posterior bag, thereby expanding the posterior bag and producing pressure upon the posterior nasal cavity.

17. The nasal catheter system of claim 16, wherein the catheter further comprises:
  a) a second anterior fluid channel having a second anterior output opening, a second anterior input port, and a second external section; and
  b) a second anterior bag attached to the second anterior fluid channel, the second anterior bag having a second anterior chamber, a second outer surface, a second front end, a second middle portion and a second rear end, and a plurality of second anterior capillary tubes having an second open end and a second closed end and attached to the second outer surface, taking the form of finger-like projections extending generally perpendicular from the second outer surface and spanning over about the second middle portion, the plurality of second anterior capillary tubes having a plurality of second anterior capillary tube cavities, wherein the second open end of the second anterior capillary tube cavities are in communication with the second anterior chamber;
    whereby the nasal catheter system may be inserted into a second anterior nasal cavity and when the catheter is filled with a fluid, the fluid flows through the second anterior fluid channel and into the second anterior bag, thereby expanding the second anterior bag and producing pressure upon the second anterior nasal cavity.

18. The nasal catheter system of claim 17 wherein the catheter further comprises of:
  a) an elongated section;
    wherein the elongated section may be inserted through the second anterior nasal cavity, the posterior nasal cavity and into the throat whereby a secondary member can be inserted through the first anterior nasal cavity, the posterior nasal cavity and into the throat, wherein the secondary member can be attached to the elongated section of the catheter, so that the secondary member is pulled back through the first anterior nasal cavity, pulling the catheter, the posterior bag, the first anterior bag and the second anterior bag into the posterior nasal cavity, first anterior nasal cavity and second anterior nasal cavity.

19. The nasal catheter system of claim 18, wherein the posterior fluid channel has a second posterior input port.

20. The nasal catheter system of claim 19, wherein the first anterior bag, second anterior bag and posterior bag are made of silicone.

21. The nasal catheter system of claim 20 wherein the plurality of first anterior capillary tubes span from about the first front end to about the first rear end including the first middle portion and the plurality of second anterior capillary tubes span from about the second front end to about the second rear end including the second middle portion.

* * * * *